(12) United States Patent
Pett et al.

(10) Patent No.: US 11,633,214 B2
(45) Date of Patent: Apr. 25, 2023

(54) VARIOUS OPERATING MECHANISMS FOR INTRAOSSEOUS ACCESS MEDICAL DEVICES AND METHODS THEREOF

(71) Applicant: Bard Access Systems, Inc., Salt Lake City, UT (US)

(72) Inventors: Daniel Pett, Sandy, UT (US); Daniel B. Blanchard, Bountiful, UT (US); Eric W. Lindekugel, Salt Lake City, UT (US); Joe Spataro, Cottonwood Heights, UT (US); Ralph Sonderegger, Farmington, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 182 days.

(21) Appl. No.: 17/035,336

(22) Filed: Sep. 28, 2020

(65) Prior Publication Data
US 2021/0093357 A1 Apr. 1, 2021

Related U.S. Application Data
(60) Provisional application No. 62/907,460, filed on Sep. 27, 2019.

(51) Int. Cl.
*A61B 17/34* (2006.01)
(52) U.S. Cl.
CPC ...... *A61B 17/3472* (2013.01); *A61B 17/3478* (2013.01)
(58) Field of Classification Search
CPC .................................................. A61B 17/3472
See application file for complete search history.

(56) References Cited

U.S. PATENT DOCUMENTS 2,773,501 A 12/1956 Young
3,071,135 A 1/1963 Baldwin et al.
(Continued)

FOREIGN PATENT DOCUMENTS

CN 108742795 A 11/2018
CN 110547847 A 12/2019
(Continued)

OTHER PUBLICATIONS

PCT/US2021/ 046573 filed Aug. 18, 2021 International Search Report and Written Opinion dated Nov. 30, 2021.
(Continued)

*Primary Examiner* — Nicholas W Woodall
(74) *Attorney, Agent, or Firm* — Rutan & Tucker LLP

(57) ABSTRACT

Disclosed herein are intraosseous access devices having various operating mechanisms, as well as methods of the intraosseous access devices. For example, an intraosseous access device includes, in some embodiments, a constant-torque spring assembly, a drive shaft, an intraosseous needle, and an interlock mechanism. The constant-torque spring assembly is disposed in a housing, and the drive shaft extends from the housing. The drive shaft is coupled to the constant-torque spring assembly. The intraosseous needle is coupled to the drive shaft. The intraosseous needle is configured for drilling through bone and providing intraosseous access to a medullary cavity of a patient. The interlock mechanism is configured to prevent rotation of the intraosseous needle and the drilling therewith until the interlock mechanism is disengaged.

24 Claims, 13 Drawing Sheets

(56) References Cited

U.S. PATENT DOCUMENTS

| | | |
|---|---|---|
| 3,804,544 A | 4/1974 | Adams |
| 3,811,442 A | 5/1974 | Maroth |
| 3,815,605 A | 6/1974 | Schmidt et al. |
| 3,991,765 A | 11/1976 | Cohen |
| 4,266,555 A | 5/1981 | Jamshidi |
| 4,314,565 A | 2/1982 | Lee |
| 4,383,530 A | 5/1983 | Bruno |
| 4,736,742 A | 4/1988 | Alexson et al. |
| 4,889,529 A | 12/1989 | Haindl |
| 4,952,207 A | 8/1990 | Lemieux |
| 4,964,854 A | 10/1990 | Luther |
| 4,969,870 A | 11/1990 | Kramer et al. |
| 5,040,542 A | 8/1991 | Gray |
| 5,042,558 A | 8/1991 | Hussey et al. |
| 5,053,017 A | 10/1991 | Chamuel |
| 5,122,114 A | 6/1992 | Miller et al. |
| 5,207,697 A | 5/1993 | Carusillo et al. |
| 5,263,939 A | 11/1993 | Wortrich |
| 5,290,267 A | 3/1994 | Zimmermann |
| 5,312,364 A | 5/1994 | Jacobs |
| 5,332,398 A | 7/1994 | Miller et al. |
| 5,364,367 A | 11/1994 | Banks et al. |
| 5,372,583 A | 12/1994 | Roberts et al. |
| 5,406,940 A | 4/1995 | Melzer et al. |
| 5,451,210 A | 9/1995 | Kramer et al. |
| 5,554,154 A | 9/1996 | Rosenberg |
| 5,575,780 A | 11/1996 | Saito |
| 5,591,188 A | 1/1997 | Waisman |
| 5,601,559 A | 2/1997 | Melker et al. |
| 5,667,509 A | 9/1997 | Westin |
| 5,688,249 A | 11/1997 | Chang et al. |
| 5,779,708 A | 7/1998 | Wu |
| 5,817,052 A | 10/1998 | Johnson et al. |
| 5,853,393 A | 12/1998 | Bogert |
| 5,868,711 A | 2/1999 | Kramer et al. |
| 5,885,293 A | 3/1999 | McDevitt |
| 5,927,976 A | 7/1999 | Wu |
| 5,960,797 A | 10/1999 | Kramer et al. |
| 5,967,143 A | 10/1999 | Klappenberger |
| 6,117,108 A | 9/2000 | Woehr et al. |
| 6,135,769 A | 10/2000 | Kwan |
| 6,199,664 B1 | 3/2001 | Tkaczyk et al. |
| 6,210,373 B1 | 4/2001 | Allmon |
| 6,228,088 B1 | 5/2001 | Miller et al. |
| 6,247,928 B1 | 6/2001 | Meller et al. |
| 6,270,484 B1 | 8/2001 | Yoon |
| 6,273,715 B1 | 8/2001 | Meller et al. |
| 6,419,490 B1 | 7/2002 | Kitchings Weathers, Jr. |
| 6,458,117 B1 | 10/2002 | Pollins, Sr. |
| 6,527,778 B2 | 3/2003 | Athanasiou et al. |
| 6,602,214 B2 | 8/2003 | Heinz et al. |
| 6,626,887 B1 | 9/2003 | Wu |
| 6,629,959 B2 | 10/2003 | Kuracina et al. |
| 6,641,395 B2 | 11/2003 | Kumar et al. |
| 6,652,490 B2 | 11/2003 | Howell |
| 6,692,471 B2 | 2/2004 | Boudreaux |
| 6,761,726 B1 | 7/2004 | Findlay et al. |
| 6,814,734 B2 | 11/2004 | Chappuis et al. |
| 6,830,562 B2 | 12/2004 | Mogensen et al. |
| 6,875,219 B2 | 4/2005 | Arramon et al. |
| 6,905,486 B2 | 6/2005 | Gibbs |
| 6,916,292 B2 | 7/2005 | Morawski et al. |
| 6,984,213 B2 | 1/2006 | Horner et al. |
| 6,997,907 B2 | 2/2006 | Safabash et al. |
| 7,112,191 B2 | 9/2006 | Daga |
| 7,135,031 B2 | 11/2006 | Flint |
| 7,214,208 B2 | 5/2007 | Vaillancourt et al. |
| 7,347,838 B2 | 3/2008 | Kulli |
| 7,347,840 B2 | 3/2008 | Findlay et al. |
| 7,407,493 B2 | 8/2008 | Cane' |
| 7,458,954 B2 | 12/2008 | Ferguson et al. |
| 7,513,888 B2 | 4/2009 | Sircom et al. |
| 7,530,965 B2 | 5/2009 | Villa et al. |
| 7,534,227 B2 | 5/2009 | Kulli |
| 7,569,033 B2 | 8/2009 | Greene et al. |
| 7,582,102 B2 | 9/2009 | Heinz et al. |
| 7,588,559 B2 | 9/2009 | Aravena et al. |
| 7,658,725 B2 | 2/2010 | Bialecki et al. |
| 7,670,328 B2 | 3/2010 | Miller |
| 7,699,807 B2 | 4/2010 | Faust et al. |
| 7,699,850 B2 | 4/2010 | Miller |
| 7,736,332 B2 | 6/2010 | Carlyon et al. |
| 7,749,225 B2 | 7/2010 | Chappuis et al. |
| 7,798,994 B2 | 9/2010 | Brimhall |
| 7,811,260 B2 | 10/2010 | Miller et al. |
| 7,815,642 B2 | 10/2010 | Miller |
| 7,828,774 B2 | 11/2010 | Harding et al. |
| 7,833,204 B2 | 11/2010 | Picha |
| 7,842,038 B2 | 11/2010 | Haddock et al. |
| 7,850,620 B2 | 12/2010 | Miller et al. |
| 7,850,650 B2 | 12/2010 | Breitweiser |
| D633,199 S | 2/2011 | MacKay et al. |
| 7,899,528 B2 | 3/2011 | Miller et al. |
| 7,905,857 B2 | 3/2011 | Swisher |
| 7,951,089 B2 | 5/2011 | Miller |
| 7,955,297 B2 | 6/2011 | Radmer et al. |
| 7,972,339 B2 | 7/2011 | Nassiri et al. |
| 7,976,502 B2 | 7/2011 | Baid |
| 8,038,664 B2 | 10/2011 | Miller et al. |
| 8,043,253 B2 | 10/2011 | Kraft et al. |
| 8,043,265 B2 | 10/2011 | Abe et al. |
| 8,142,365 B2 | 3/2012 | Miller |
| 8,152,771 B2 | 4/2012 | Mogensen et al. |
| 8,162,904 B2 | 4/2012 | Takano et al. |
| 8,167,899 B2 | 5/2012 | Justis et al. |
| 8,235,945 B2 | 8/2012 | Baid |
| 8,246,584 B2 | 8/2012 | Aravena et al. |
| 8,273,053 B2 | 9/2012 | Saltzstein |
| 8,292,891 B2 | 10/2012 | Browne et al. |
| 8,308,693 B2 | 11/2012 | Miller et al. |
| 8,333,769 B2 | 12/2012 | Browne et al. |
| 8,356,598 B2 | 1/2013 | Rumsey |
| 8,357,163 B2 | 1/2013 | Sidebotham et al. |
| 8,388,541 B2 | 3/2013 | Messerly et al. |
| 8,388,623 B2 | 3/2013 | Browne et al. |
| 8,414,539 B1 | 4/2013 | Kuracina et al. |
| 8,419,683 B2 | 4/2013 | Miller et al. |
| 8,480,632 B2 | 7/2013 | Miller et al. |
| 8,480,672 B2 | 7/2013 | Browne et al. |
| 8,486,027 B2 | 7/2013 | Findlay et al. |
| 8,506,568 B2 | 8/2013 | Miller |
| 8,535,271 B2 | 9/2013 | Fuchs et al. |
| 8,562,615 B2 | 10/2013 | Browne et al. |
| 8,641,715 B2 | 2/2014 | Miller |
| 8,647,257 B2 | 2/2014 | Jansen et al. |
| 8,656,929 B2 | 2/2014 | Miller et al. |
| 8,657,790 B2 | 2/2014 | Tai et al. |
| 8,663,231 B2 | 3/2014 | Browne et al. |
| 8,668,698 B2 | 3/2014 | Miller et al. |
| 8,684,978 B2 | 4/2014 | Miller et al. |
| 8,690,791 B2 | 4/2014 | Miller |
| 8,715,287 B2 | 5/2014 | Miller |
| 8,771,230 B2 | 7/2014 | White et al. |
| 8,781,555 B2 | 7/2014 | Burnside et al. |
| 8,801,663 B2 | 8/2014 | Woehr |
| 8,812,101 B2 | 8/2014 | Miller et al. |
| 8,814,835 B2 | 8/2014 | Baid |
| 8,821,493 B2 | 9/2014 | Anderson |
| 8,828,001 B2 | 9/2014 | Stearns et al. |
| 8,849,382 B2 | 9/2014 | Cox et al. |
| 8,870,872 B2 | 10/2014 | Miller |
| 8,936,575 B2 | 1/2015 | Moulton |
| 8,944,069 B2 | 2/2015 | Miller et al. |
| 8,974,410 B2 | 3/2015 | Miller et al. |
| 8,998,848 B2 | 4/2015 | Miller et al. |
| 9,072,543 B2 | 7/2015 | Miller et al. |
| 9,078,637 B2 | 7/2015 | Miller |
| 9,149,625 B2 | 10/2015 | Woehr et al. |
| 9,173,679 B2 | 11/2015 | Tzachar et al. |
| 9,226,756 B2 | 1/2016 | Teisen et al. |
| 9,278,195 B2 | 3/2016 | Erskine |
| 9,295,487 B2 | 3/2016 | Miller et al. |
| 9,302,077 B2 | 4/2016 | Domonkos et al. |
| 9,314,232 B2 | 4/2016 | Stark |

(56) References Cited

U.S. PATENT DOCUMENTS

| | | |
|---|---|---|
| 9,314,270 B2 | 4/2016 | Miller |
| 9,358,348 B2 | 6/2016 | Weilbacher et al. |
| 9,393,031 B2 | 7/2016 | Miller |
| 9,414,815 B2 | 8/2016 | Miller et al. |
| 9,415,192 B2 | 8/2016 | Kuracina et al. |
| 9,421,345 B2 | 8/2016 | Woehr et al. |
| 9,427,555 B2 | 8/2016 | Baid |
| 9,433,400 B2 | 9/2016 | Miller |
| 9,439,667 B2 | 9/2016 | Miller |
| 9,439,702 B2 | 9/2016 | Arthur et al. |
| 9,445,743 B2 | 9/2016 | Kassab |
| 9,451,968 B2 | 9/2016 | Miller et al. |
| 9,451,983 B2 | 9/2016 | Windolf |
| 9,456,766 B2 | 10/2016 | Cox et al. |
| 9,480,483 B2 | 11/2016 | Browne et al. |
| 9,492,097 B2 | 11/2016 | Wilkes et al. |
| 9,504,477 B2 | 11/2016 | Miller et al. |
| 9,521,961 B2 | 12/2016 | Silverstein et al. |
| 9,545,243 B2 | 1/2017 | Miller et al. |
| 9,554,716 B2 | 1/2017 | Burnside et al. |
| 9,615,816 B2 | 4/2017 | Woodard |
| 9,615,838 B2 | 4/2017 | Nino et al. |
| 9,623,210 B2 | 4/2017 | Woehr |
| 9,636,031 B2 | 5/2017 | Cox |
| 9,636,484 B2 | 5/2017 | Baid |
| 9,649,048 B2 | 5/2017 | Cox et al. |
| 9,681,889 B1 | 6/2017 | Greenhalgh et al. |
| 9,687,633 B2 | 6/2017 | Teoh |
| 9,717,564 B2 | 8/2017 | Miller et al. |
| 9,730,729 B2 | 8/2017 | Kilcoin et al. |
| 9,782,546 B2 | 10/2017 | Woehr |
| 9,839,740 B2 | 12/2017 | Beamer et al. |
| 9,844,646 B2 | 12/2017 | Knutsson |
| 9,844,647 B2 | 12/2017 | Knutsson |
| 9,872,703 B2 | 1/2018 | Miller et al. |
| 9,883,853 B2 | 2/2018 | Woodard et al. |
| 9,895,512 B2 | 2/2018 | Kraft et al. |
| 9,962,211 B2 | 5/2018 | Csernatoni |
| 10,052,111 B2 | 8/2018 | Miller et al. |
| 10,092,320 B2 | 10/2018 | Morgan et al. |
| 10,159,531 B2 | 12/2018 | Misener et al. |
| 10,172,538 B2 | 1/2019 | Kassab |
| 10,413,211 B2 | 9/2019 | Kassab |
| 10,449,330 B2 | 10/2019 | Newman et al. |
| 10,893,887 B2 | 1/2021 | Blanchard |
| 10,980,522 B2 | 4/2021 | Muse |
| 2003/0060781 A1 | 3/2003 | Mogensen et al. |
| 2003/0225344 A1 | 12/2003 | Miller |
| 2003/0225411 A1 | 12/2003 | Miller |
| 2003/0229308 A1 | 12/2003 | Tsals et al. |
| 2004/0010236 A1 | 1/2004 | Morawski et al. |
| 2004/0059317 A1 | 3/2004 | Hermann |
| 2004/0220497 A1 | 11/2004 | Findlay et al. |
| 2004/0243135 A1 | 12/2004 | Koseki |
| 2005/0035014 A1 | 2/2005 | Cane |
| 2005/0101912 A1 | 5/2005 | Faust et al. |
| 2005/0113866 A1 | 5/2005 | Heinz et al. |
| 2005/0131345 A1* | 6/2005 | Miller ................ A61B 17/3476 604/117 |
| 2006/0015066 A1 | 1/2006 | Turieo et al. |
| 2006/0025723 A1 | 2/2006 | Ballarini |
| 2007/0049945 A1 | 3/2007 | Miller |
| 2007/0191772 A1 | 8/2007 | Wojcik |
| 2007/0270775 A1 | 11/2007 | Miller et al. |
| 2008/0015467 A1 | 1/2008 | Miller |
| 2008/0154304 A1 | 6/2008 | Crawford et al. |
| 2008/0208136 A1 | 8/2008 | Findlay et al. |
| 2008/0215056 A1 | 9/2008 | Miller et al. |
| 2008/0221580 A1 | 9/2008 | Miller et al. |
| 2008/0257359 A1 | 10/2008 | Rumsey |
| 2009/0048575 A1 | 2/2009 | Waters |
| 2009/0054808 A1 | 2/2009 | Miller |
| 2009/0093830 A1 | 4/2009 | Miller |
| 2009/0204024 A1 | 8/2009 | Miller |
| 2009/0306697 A1 | 12/2009 | Fischvogt |
| 2010/0004606 A1* | 1/2010 | Hansen ................ A61F 2/966 604/264 |
| 2010/0204649 A1 | 8/2010 | Miller et al. |
| 2010/0286607 A1 | 11/2010 | Saltzstein |
| 2010/0298830 A1 | 11/2010 | Browne et al. |
| 2010/0298831 A1 | 11/2010 | Browne et al. |
| 2010/0312246 A1 | 12/2010 | Browne et al. |
| 2011/0004163 A1 | 1/2011 | Vaidya |
| 2011/0028976 A1* | 2/2011 | Miller .............. A61B 17/32053 600/567 |
| 2012/0202180 A1 | 8/2012 | Stock et al. |
| 2012/0203154 A1 | 8/2012 | Tzachar |
| 2012/0274280 A1 | 11/2012 | Yip et al. |
| 2013/0030439 A1 | 1/2013 | Browne et al. |
| 2013/0041345 A1 | 2/2013 | Kilcoin et al. |
| 2013/0072938 A1 | 3/2013 | Browne et al. |
| 2013/0102924 A1 | 4/2013 | Findlay et al. |
| 2013/0158484 A1 | 6/2013 | Browne et al. |
| 2013/0178807 A1 | 7/2013 | Baid |
| 2014/0031674 A1 | 1/2014 | Newman et al. |
| 2014/0031794 A1 | 1/2014 | Windolf |
| 2014/0039400 A1 | 2/2014 | Browne et al. |
| 2014/0081281 A1 | 3/2014 | Felder |
| 2014/0142577 A1 | 5/2014 | Miller |
| 2014/0188133 A1 | 7/2014 | Misener |
| 2014/0262408 A1 | 9/2014 | Woodard |
| 2014/0262880 A1 | 9/2014 | Yoon |
| 2014/0276205 A1 | 9/2014 | Miller et al. |
| 2014/0276206 A1* | 9/2014 | Woodward ............... B23Q 3/12 600/564 |
| 2014/0276471 A1 | 9/2014 | Emery et al. |
| 2014/0276833 A1 | 9/2014 | Larsen et al. |
| 2014/0276839 A1 | 9/2014 | Forman et al. |
| 2014/0343454 A1 | 11/2014 | Miller et al. |
| 2014/0343497 A1 | 11/2014 | Baid |
| 2015/0011941 A1 | 1/2015 | Saeki |
| 2015/0045732 A1 | 2/2015 | Murphy et al. |
| 2015/0080762 A1 | 3/2015 | Kassab et al. |
| 2015/0126931 A1 | 5/2015 | Holm et al. |
| 2015/0196737 A1 | 7/2015 | Baid |
| 2015/0223786 A1 | 8/2015 | Morgan et al. |
| 2015/0230823 A1 | 8/2015 | Morgan et al. |
| 2015/0238733 A1 | 8/2015 | bin Abdulla |
| 2015/0342615 A1 | 12/2015 | Keinan et al. |
| 2015/0342756 A1 | 12/2015 | Bays et al. |
| 2015/0351797 A1 | 12/2015 | Miller et al. |
| 2015/0366569 A1 | 12/2015 | Miller |
| 2016/0022282 A1 | 1/2016 | Miller et al. |
| 2016/0022284 A1 | 1/2016 | Lele et al. |
| 2016/0058432 A1 | 3/2016 | Miller |
| 2016/0066954 A1 | 3/2016 | Miller et al. |
| 2016/0136410 A1 | 5/2016 | Aklog et al. |
| 2016/0183974 A1 | 6/2016 | Miller |
| 2016/0184509 A1 | 6/2016 | Miller et al. |
| 2016/0235949 A1 | 8/2016 | Baid |
| 2016/0354539 A1 | 12/2016 | Tan et al. |
| 2016/0361519 A1 | 12/2016 | Teoh et al. |
| 2017/0020533 A1 | 1/2017 | Browne et al. |
| 2017/0020560 A1 | 1/2017 | Van Citters et al. |
| 2017/0021138 A1 | 1/2017 | Sokolski |
| 2017/0043135 A1 | 2/2017 | Knutsson |
| 2017/0105763 A1 | 4/2017 | Karve et al. |
| 2017/0136217 A1 | 5/2017 | Riesenberger et al. |
| 2017/0151419 A1 | 6/2017 | Sonksen |
| 2017/0156740 A9 | 6/2017 | Stark |
| 2017/0156751 A1 | 6/2017 | Csernatoni |
| 2017/0209129 A1 | 7/2017 | Fagundes et al. |
| 2017/0231644 A1 | 8/2017 | Anderson |
| 2017/0303962 A1 | 10/2017 | Browne et al. |
| 2017/0303963 A1 | 10/2017 | Kilcoin et al. |
| 2018/0049772 A1* | 2/2018 | Brockman ......... A61B 17/8811 |
| 2018/0092662 A1 | 4/2018 | Rioux et al. |
| 2018/0116551 A1 | 5/2018 | Newman et al. |
| 2018/0116642 A1 | 5/2018 | Woodard et al. |
| 2018/0116693 A1 | 5/2018 | Blanchard et al. |
| 2018/0117262 A1 | 5/2018 | Islam |
| 2018/0125465 A1 | 5/2018 | Muse et al. |
| 2018/0154112 A1 | 6/2018 | Chan et al. |
| 2018/0221003 A1 | 8/2018 | Hibner et al. |

(56) References Cited

U.S. PATENT DOCUMENTS

| | | | |
|---|---|---|---|
| 2018/0228509 A1* | 8/2018 | Fojtik | A61B 17/3472 |
| 2018/0242982 A1 | 8/2018 | Laughlin et al. | |
| 2019/0069812 A1 | 3/2019 | Isaacson et al. | |
| 2019/0282244 A1 | 9/2019 | Muse | |
| 2020/0054347 A1 | 2/2020 | Coppedge et al. | |
| 2020/0054410 A1 | 2/2020 | Pfotenhauer et al. | |
| 2020/0113584 A1 | 4/2020 | McGinley et al. | |
| 2020/0129186 A1 | 4/2020 | Miller et al. | |
| 2020/0197121 A1 | 6/2020 | Morey et al. | |
| 2021/0093358 A1 | 4/2021 | Lindekugel et al. | |
| 2021/0322055 A1 | 10/2021 | Lindekugel et al. | |
| 2021/0375445 A1 | 12/2021 | Lindekugel et al. | |
| 2022/0240976 A1 | 8/2022 | Pett et al. | |
| 2022/0249104 A1 | 8/2022 | Pett et al. | |

FOREIGN PATENT DOCUMENTS

| | | |
|---|---|---|
| EP | 0923961 A1 | 6/1999 |
| ES | 2390297 A1 | 11/2012 |
| FR | 2581548 A1 | 11/1986 |
| JP | 2018509969 A | 4/2018 |
| WO | 1997024151 A1 | 7/1997 |
| WO | 1998052638 A3 | 2/1999 |
| WO | 2005/046769 A2 | 5/2005 |
| WO | 05041790 A2 | 5/2005 |
| WO | 2005053506 A2 | 6/2005 |
| WO | 2005072625 A2 | 8/2005 |
| WO | 2007018809 A2 | 2/2007 |
| WO | 2008002961 A2 | 1/2008 |
| WO | 2008016757 A2 | 2/2008 |
| WO | 08033873 A2 | 3/2008 |
| WO | 2008033871 A2 | 3/2008 |
| WO | 2008033872 A2 | 3/2008 |
| WO | 2008033874 A2 | 3/2008 |
| WO | 2008054894 A2 | 5/2008 |
| WO | 2008086258 A1 | 7/2008 |
| WO | 2008124206 A2 | 10/2008 |
| WO | 2008124463 A2 | 10/2008 |
| WO | 2008130893 A1 | 10/2008 |
| WO | 2008134355 A2 | 11/2008 |
| WO | 2008144379 A2 | 11/2008 |
| WO | 2009070896 A1 | 6/2009 |
| WO | 2010043043 A2 | 4/2010 |
| WO | 2011097311 A2 | 8/2011 |
| WO | 2011139294 A1 | 11/2011 |
| WO | 2013009901 A2 | 1/2013 |
| WO | 2013173360 A1 | 11/2013 |
| WO | 2014142948 A1 | 9/2014 |
| WO | 2014144239 A1 | 9/2014 |
| WO | 2014144262 A1 | 9/2014 |
| WO | 2014144489 A2 | 9/2014 |
| WO | 2014144757 A1 | 9/2014 |
| WO | 2014144797 A1 | 9/2014 |
| WO | 2015/177612 A1 | 11/2015 |
| WO | 16033016 A1 | 3/2016 |
| WO | 16053834 A1 | 4/2016 |
| WO | 2016/085973 A1 | 6/2016 |
| WO | 2016163939 A1 | 10/2016 |
| WO | 18006045 A1 | 1/2018 |
| WO | 2018025094 A1 | 2/2018 |
| WO | 2018058036 A1 | 3/2018 |
| WO | 2018075694 A1 | 4/2018 |
| WO | 18098086 A1 | 5/2018 |
| WO | 2018165334 A1 | 9/2018 |
| WO | 2018165339 A1 | 9/2018 |
| WO | 2019051343 A1 | 3/2019 |
| WO | 2019/164990 A1 | 8/2019 |
| WO | 2021/011795 A1 | 1/2021 |
| WO | 2021/016122 A1 | 1/2021 |
| WO | 2021/062385 A1 | 4/2021 |
| WO | 2021062038 A1 | 4/2021 |
| WO | 2021062394 A1 | 4/2021 |
| WO | 2022/165232 A1 | 8/2022 |

OTHER PUBLICATIONS

PCT/US2021/ 047378 filed Aug. 24, 2021 International Search Report and Written Opinion dated Nov. 17, 2021.

PCT/US2021/ 048542 filed Aug. 31, 2021 International Search Report and Written Opinion dated Dec. 9, 2021.

PCT/US2021/ 049475 filed Sep. 8, 2021 International Search Report and Written Opinion dated Dec. 9, 2021.

U.S. Appl. No. 17/031,650, filed Sep. 24, 2020 Non-Final Office Action dated Jan. 19, 2022.

Ekchian Gregory James et al: "Quantitative Methods for In Vitro and In Vivo Characterization of Cell and Tissue Metabolism", Jun. 11, 2018, XP055839281, retrieved from the internet on Sep. 8, 2021 : URL: https://dspace.mit.edu/bitstream/handle/1721.1/117890/1051211749-MIT.pdf?sequence=1&isAllowed-y.

PCT/US2021/ 035232 filed Jun. 1, 2021 International Search Report and Written Opinion dated Oct. 19, 2021.

PCT/US2021/035475 filed Jun. 2, 2021 International Search Report and Written Opinion dated Sep. 17, 2021.

PCT/US2021/028114 filed Apr. 20, 2021 International Search Report and Written Opinion dated Jul. 12, 2021.

PCT/US2020/ 053119 filed Sep. 28, 2020 International Search Report and Written Opinion dated Jan. 5, 2021.

PCT/US2020/052558 filed Sep. 24, 2020 International Search Report and Written Opinion dated Feb. 11, 2021.

PCT/US2020/053135 filed Sep. 28, 2020 International Search Report and Written Opinion dated Dec. 18, 2020.

PCT/US2022/014391 filed Jan. 28, 2022 International Search Report and Written Opinion dated Apr. 14, 2022.

PCT/US2022/015686 filed Feb. 8, 2022 International Search Report and Written Opinion dated May 25, 2022.

U.S. Appl. No. 17/031,650, filed Sep. 24, 2020 Final Office Action dated Jul. 20, 2022.

PCT/US2019/ 018828 filed Feb. 20, 2019 International Preliminary Report on Patentability dated Aug. 27, 2020.

PCT/US2019/ 018828 filed Feb. 20, 2019 International Search Report and Written Opinion dated Jun. 13, 2019.

* cited by examiner

VARIOUS OPERATING MECHANISMS FOR INTRAOSSEOUS ACCESS MEDICAL DEVICES AND METHODS THEREOF

PRIORITY

This application claims the benefit of priority to U.S. Provisional Application No. 62/907,460, filed Sep. 27, 2019, which is incorporated by reference in its entirety into this application.

BACKGROUND

Peripheral intravenous catheter ("PIVC") insertions are increasingly challenging in emergency scenarios as critically ill patients deteriorate. Intraosseous ("IO") access is often the only means available to clinicians to increase the patients' chances of recovery and even save the patients' lives. IO access can be acquired in as little as 2-5 seconds with a relatively high chance of success.

The commercial state-of-the-art medical device for IO access is a small, drill-like device built around a relatively primitive electric motor for effectuating IO access by drilling with a needle assembly of the IO-access medical device. Some medical devices for IO access utilize linear springs to provide rotational energy for drilling, while some other 10-access medical devices even rely on a manual means for providing the rotational energy for the drilling. No matter what means for drilling a clinician uses for IO access, the clinician needs to be able to control the IO-access medical device under any circumstance and interrupt the drilling at any time for any reason. In addition, there is a need to prevent accidental triggering of IO-access medical devices while handling an IO-access medical device, before the needle assembly of an IO-access medical device is properly positioned for IO access, or even while the IO-access medical device is stored, for example, in an emergency bag.

Disclosed herein are various operating mechanisms for IO-access medical devices and methods thereof that address the foregoing needs. In addition, constant-torque IO access devices and methods thereof are disclosed that significantly reduce design and manufacturing complexity of the small, drill-like devices that are currently the state-of-the-art for IO access.

SUMMARY

Disclosed herein is an IO access device including, in some embodiments, a constant-torque spring assembly, a drive shaft, an IO needle, and an interlock mechanism. The constant-torque spring assembly is disposed in a housing, and the drive shaft extends from the housing. The drive shaft is coupled to the constant-torque spring assembly. The IO needle is coupled to the drive shaft. The IO needle is configured for drilling through bone and providing IO access to a medullary cavity of a patient. The interlock mechanism is configured to prevent rotation of the IO needle and the drilling therewith until the interlock mechanism is disengaged.

In some embodiments, the constant-torque spring assembly includes a metal ribbon reversely wound onto an output spool. The output spool has an axial channel. The metal ribbon is configured to wind onto a storage spool with a constant torque when the output spool is released.

In some embodiments, spindles of the output spool and the storage spool are coupled together by at least one elastomeric loop to prevent any timing-related errors between the output spool and the storage spool.

In some embodiments, the interlock mechanism includes a trigger configured to release a lock pin disposed between the trigger and the output spool. A pressure-based trigger mechanism of the IO device is configured to require the interlock mechanism to be disengaged before activation of the pressure-based trigger mechanism for rotation of the IO needle.

In some embodiments, the interlock mechanism includes a rotatable lock pin configured to block axial movement of an extension pin disposed in the axial channel of the output spool between the lock pin and the drive shaft. A pressure-based trigger mechanism of the IO device is configured to require the interlock mechanism to be disengaged before activation of the pressure-based trigger mechanism for rotation of the IO needle.

In some embodiments, the interlock mechanism includes a trigger pivotally mounted on a transversely oriented pin having trigger teeth configured to interlock with those of a distal-end portion of the output spool. A pressure-based trigger mechanism of the IO device is configured to require the interlock mechanism to be disengaged before activation of the pressure-based trigger mechanism for rotation of the IO needle.

In some embodiments, the interlock mechanism includes a spring-loaded trigger mounted in an exterior channel of the housing including an extension channel configured to allow the drive shaft to extend from the axial channel into the extension channel when the extension channel and the axial channel are aligned. A pressure-based trigger mechanism of the IO device is configured to require the interlock mechanism to be disengaged before activation of the pressure-based trigger mechanism for rotation of the IO needle.

In some embodiments, the interlock mechanism includes a pressure-based trigger configured to release a detent from a bore of the output spool. A pressure-based trigger mechanism of the IO device is configured to allow the interlock mechanism to be disengaged either before or after activation of the pressure-based trigger mechanism for rotation of the IO needle.

In some embodiments, the pressure-based trigger mechanism includes a set of housing teeth around an aperture of the housing from which the drive shaft extends, as well as a set of complementary drive-shaft teeth around the drive shaft opposing the set of housing teeth. The set of housing teeth and the set of drive-shaft teeth are engaged in an inactive state of the IO access device by a compression spring between a back side of the set of drive-shaft teeth and the output spool.

In some embodiments, the drive shaft is slidably disposed in the axial channel of the output spool such that force applied to a distal end of the IO needle simultaneously compresses the compression spring and inserts the drive shaft deeper into the axial channel. The force applied to the distal end of the IO needle disengages the set of drive-shaft teeth from the set of housing teeth and initiates an active state of the IO access device in which rotation of the IO needle is effectuated by the output spool of the constant-torque spring assembly on the drive shaft.

In some embodiments, the compression spring is configured to relax when the force applied to the distal end of the IO needle is removed. The set of drive-shaft teeth reengages with the set of housing teeth and reinitiates the inactive state of the IO access device when the force applied to the distal end of the IO needle is removed.

In some embodiments, the IO access device is configured such that entry of the IO needle into the medullary cavity of the patient automatically removes the force applied to the distal end of the IO needle.

In some embodiments, the IO access further comprises a braking system. The braking system is configured to act on the output spool to slow the metal ribbon from winding onto the storage spool.

In some embodiments, the IO needle is configured to separate from the IO access device subsequent to achieving IO access to the medullary cavity of the patient.

In some embodiments, the IO needle includes an obturator removably disposed in a cannula. The cannula has a lumen configured for at least IO infusion upon removal of the obturator.

Also disclosed herein is a method of an IO access device including, in some embodiments, a device-obtaining step, an interlock-disengaging step, a needle-inserting step, a force-applying step, and a drilling step. The device-obtaining step includes obtaining the IO access device. The interlock-disengaging step includes disengaging an interlock mechanism configured to prevent rotation of an IO needle and drilling therewith until the interlock mechanism is disengaged. The needle-inserting step includes inserting a distal end of the IO needle through skin at an insertion site of a patient. The force-applying step includes applying force to bone at the insertion site with the distal end of the IO needle. The force-applying step activates a pressure-based trigger mechanism and starts winding a metal ribbon of a constant-torque spring assembly from an output spool onto a storage spool. The winding of the metal ribbon from the output spool onto the storage spool starts rotation of the IO needle by way of a drive shaft coupled to the constant-torque spring assembly. The drilling step includes drilling through the bone until the IO needle enters a medullary cavity of the patient. IO access is achieved upon entering the medullary cavity of the patient with the IO access device.

In some embodiments, the interlock-disengaging step includes triggering a trigger to release a lock pin disposed between the trigger and the output spool. The pressure-based trigger mechanism is configured to require the interlock-disengaging step before the force-applying step to activate the pressure-based trigger mechanism.

In some embodiments, the interlock-disengaging step includes rotating a lock pin configured to block axial movement of an extension pin disposed in an axial channel of the output spool between the lock pin and the drive shaft. The pressure-based trigger mechanism is configured to require the interlock-disengaging step before the force-applying step to activate the pressure-based trigger mechanism.

In some embodiments, the interlock-disengaging step includes triggering a trigger pivotally mounted on a transversely oriented pin having trigger teeth configured to interlock with those of a distal-end portion of the output spool. The pressure-based trigger mechanism is configured to require the interlock-disengaging step before the force-applying step to activate the pressure-based trigger mechanism.

In some embodiments, the interlock-disengaging step includes triggering a spring-loaded trigger mounted in an exterior channel of a housing including an extension channel configured to allow the drive shaft to extend from an axial channel of the output spool into the extension channel when the extension channel and the axial channel are aligned. The pressure-based trigger mechanism is configured to require the interlock-disengaging step before the force-applying step to activate the pressure-based trigger mechanism.

In some embodiments, the interlock-disengaging step includes triggering a pressure-based trigger configured to release a detent from a bore of the output spool. The pressure-based trigger mechanism is configured to require the interlock-disengaging step either before or after the force-applying step to activate the pressure-based trigger mechanism.

In some embodiments, the method further includes a force-ceasing step. The force-ceasing step includes ceasing to apply the force to the bone with the distal end of the IO needle. The force-ceasing step stops the rotation of the IO needle.

In some embodiments, the force-ceasing step is manually initiated by a clinician after feeling a change in tissue density upon entering the medullary cavity of the patient. Alternatively, the force-ceasing step is automatically initiated by the pressure-based trigger mechanism after the change in the tissue density upon entering the medullary cavity of the patient.

In some embodiments, the method further includes a needle-detaching step, an obturator-removing step, a cannula-confirming step, a cannula-securing step, and an infusion-starting step. The needle-detaching step includes detaching the IO needle from a remainder of the IO access device. The obturator-removing step includes removing from the IO needle an obturator removably disposed in a cannula. The cannula-confirming step includes confirming the cannula is disposed in the medullary cavity by aspirating bone marrow through a syringe. The cannula-securing step includes securing the cannula to the patient. The infusion-starting step includes starting IO infusion as boluses with a same or different syringe.

These and other features of the concepts provided herein will become more apparent to those of skill in the art in view of the accompanying drawings and following description, which describe particular embodiments of such concepts in greater detail.

DRAWINGS

DESCRIPTION

Figure 1:
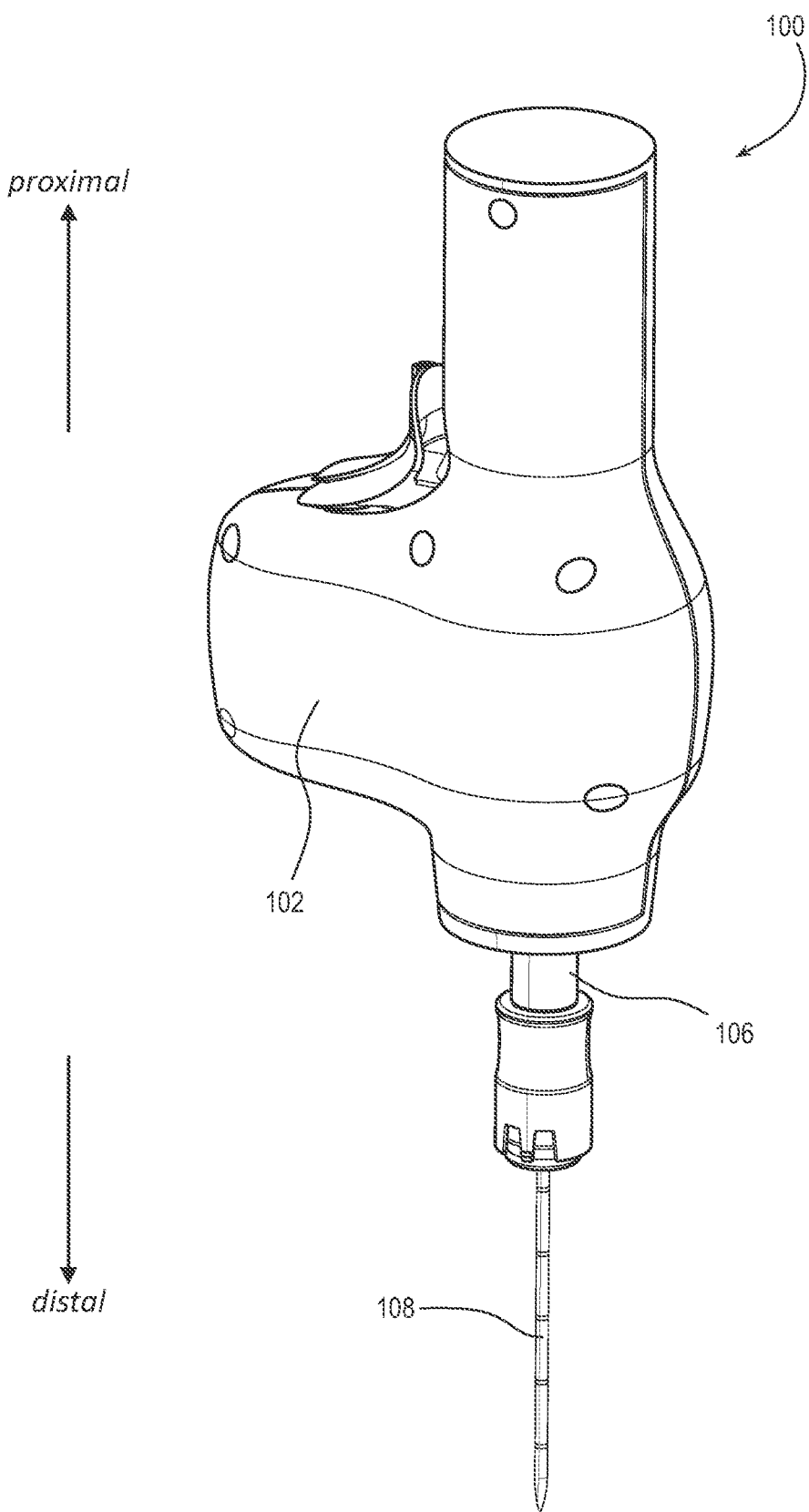
FIG. 1 illustrates a first IO access device in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need to prevent accidental triggering of IO-access medical devices while handling an IO-access medical device, before the needle assembly of an IO-access medical device is properly positioned for IO access, or even while the IO-access medical device is stored, for example, in an emergency bag. Disclosed herein are various operating mechanisms for IO-access medical devices and methods thereof that address the foregoing needs.

In addition to the foregoing, there is a need to significantly reduce design and manufacturing complexity of the small, drill-like devices that are currently the state-of-the-art for IO access. Also disclosed herein are constant-torque IO access devices and methods thereof that significantly reduce design and manufacturing complexity of the small, drill-like devices that are currently the state-of-the-art for IO access.

Various embodiments of the constant-torque IO access devices are initially described below. Various operating mechanisms such as a pressure-based trigger mechanism and a number of different interlock mechanisms for the constant-torque IO access devices are subsequently described below. Some of the various operating mechanisms are described below with respect to particular embodiments of the of the constant-torque IO access devices; however, this is for expository expediency in conveying certain concepts of the various operating mechanisms. A particular operating mechanism described with respect to a particular embodiment of a constant-torque IO access device should not be construed as being limited to the particular embodiment of the constant-torque IO access device. And while the various operating mechanisms are described in the context of constant-torque access devices, it should be understood the various operating mechanisms are not limited thereto.

IO Access Devices

Figure 5:
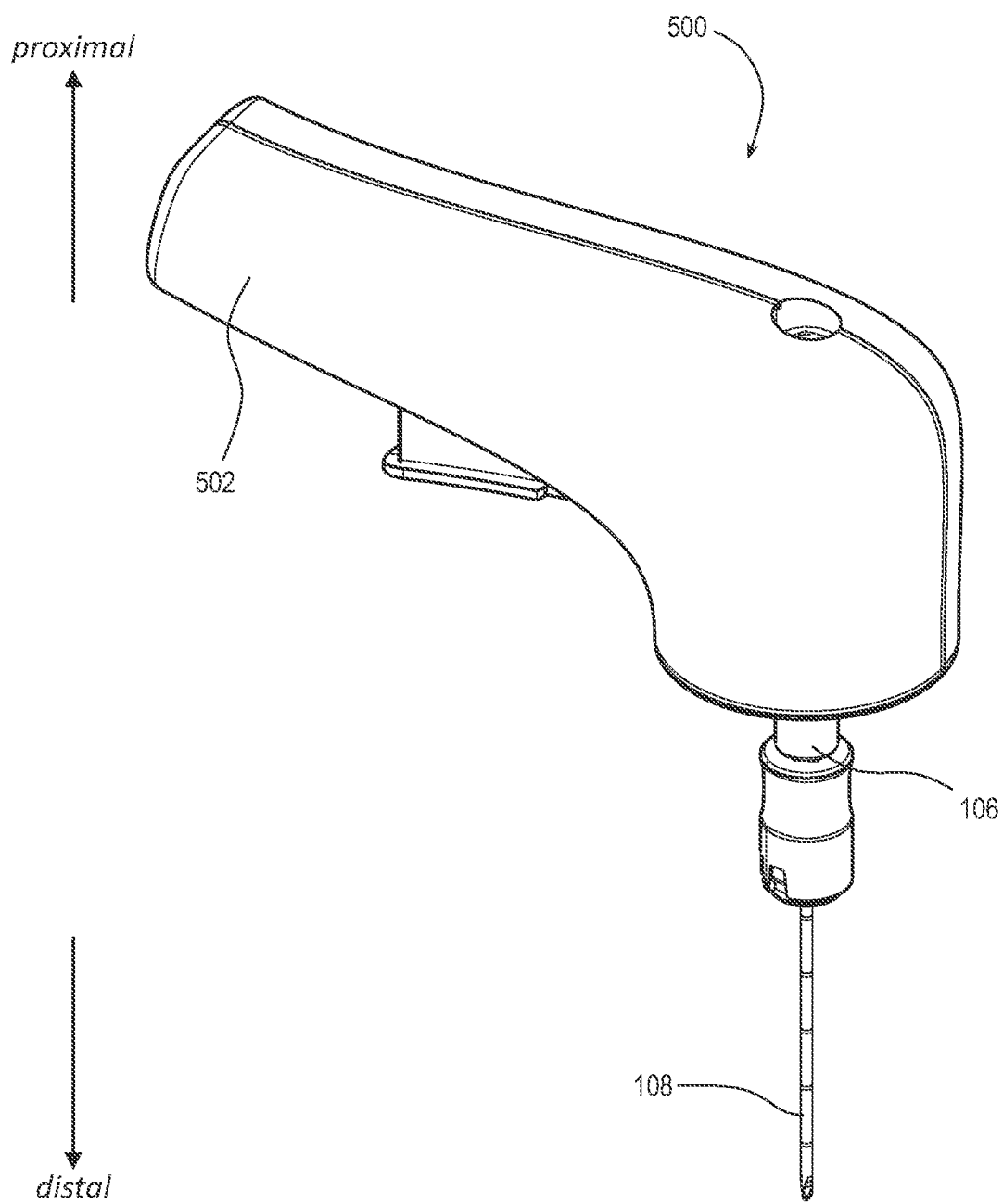
FIG. 5 illustrates a second IO access device in accordance with some embodiments.
Figure 6:
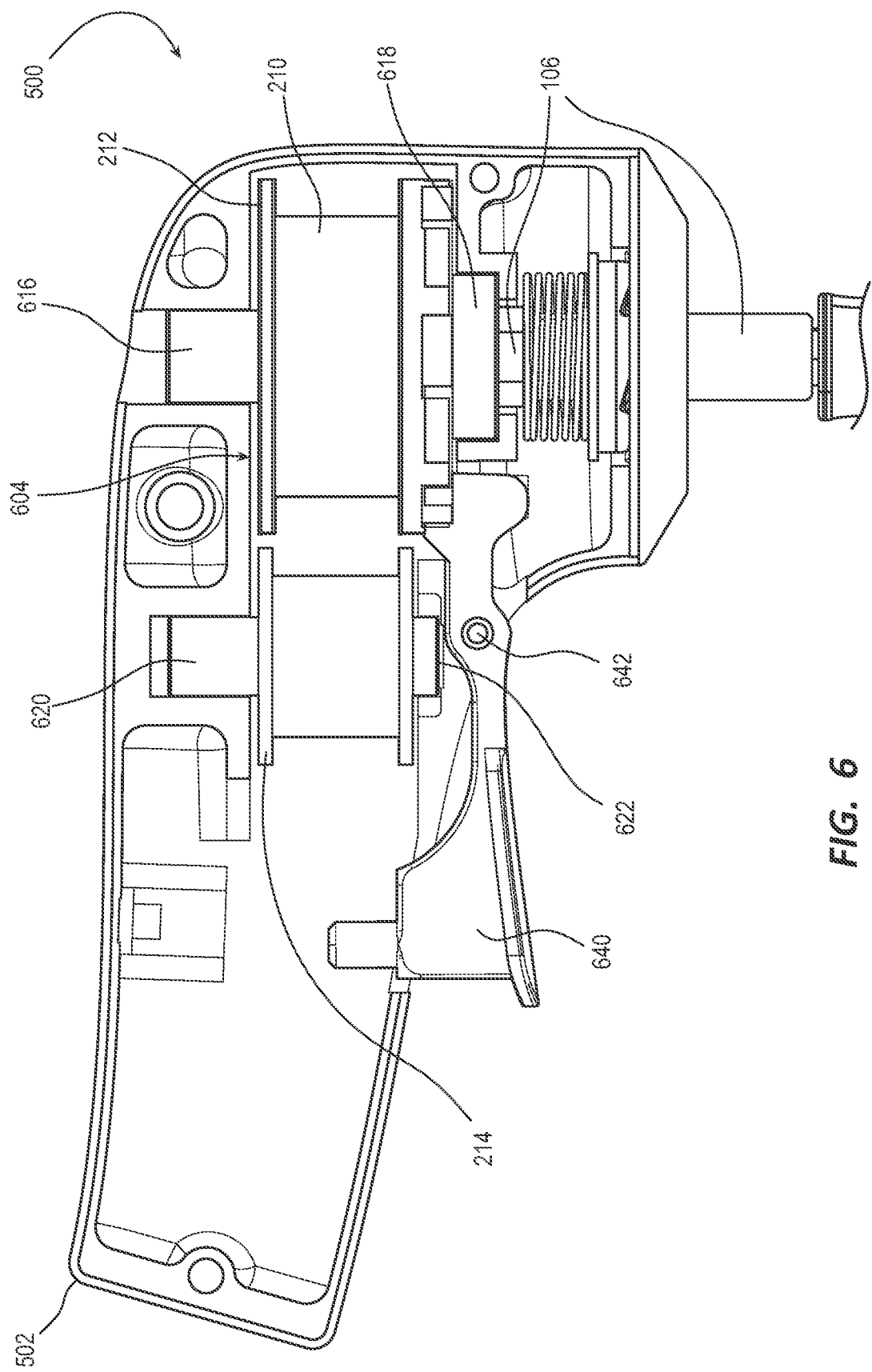
FIG. 6 illustrates the second IO access device with a side of housing removed in accordance with some embodiments.
Figure 7:
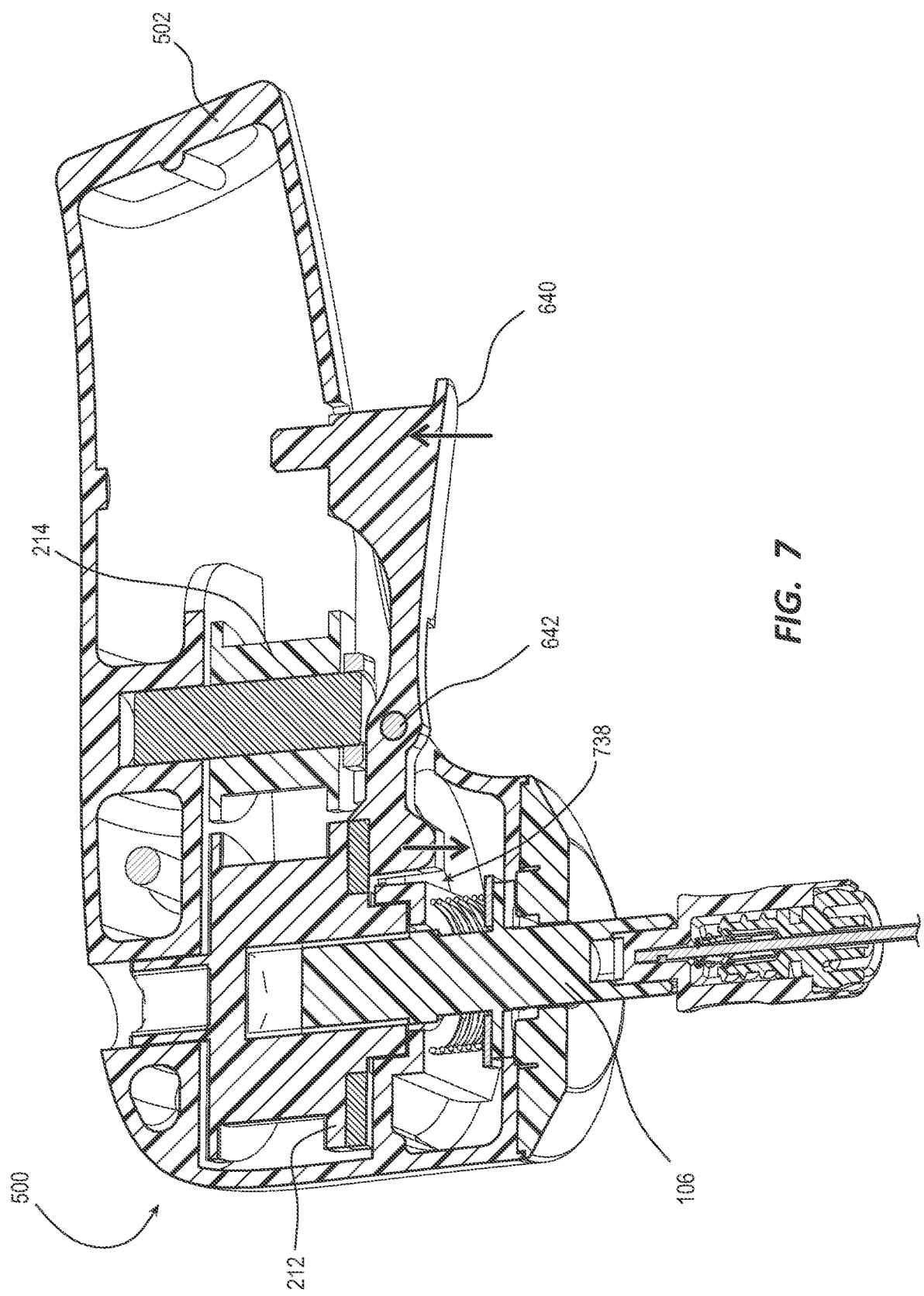
FIG. 7 illustrates a cross section of the second IO access device having an interlock mechanism in accordance with some embodiments.
Figure 10:
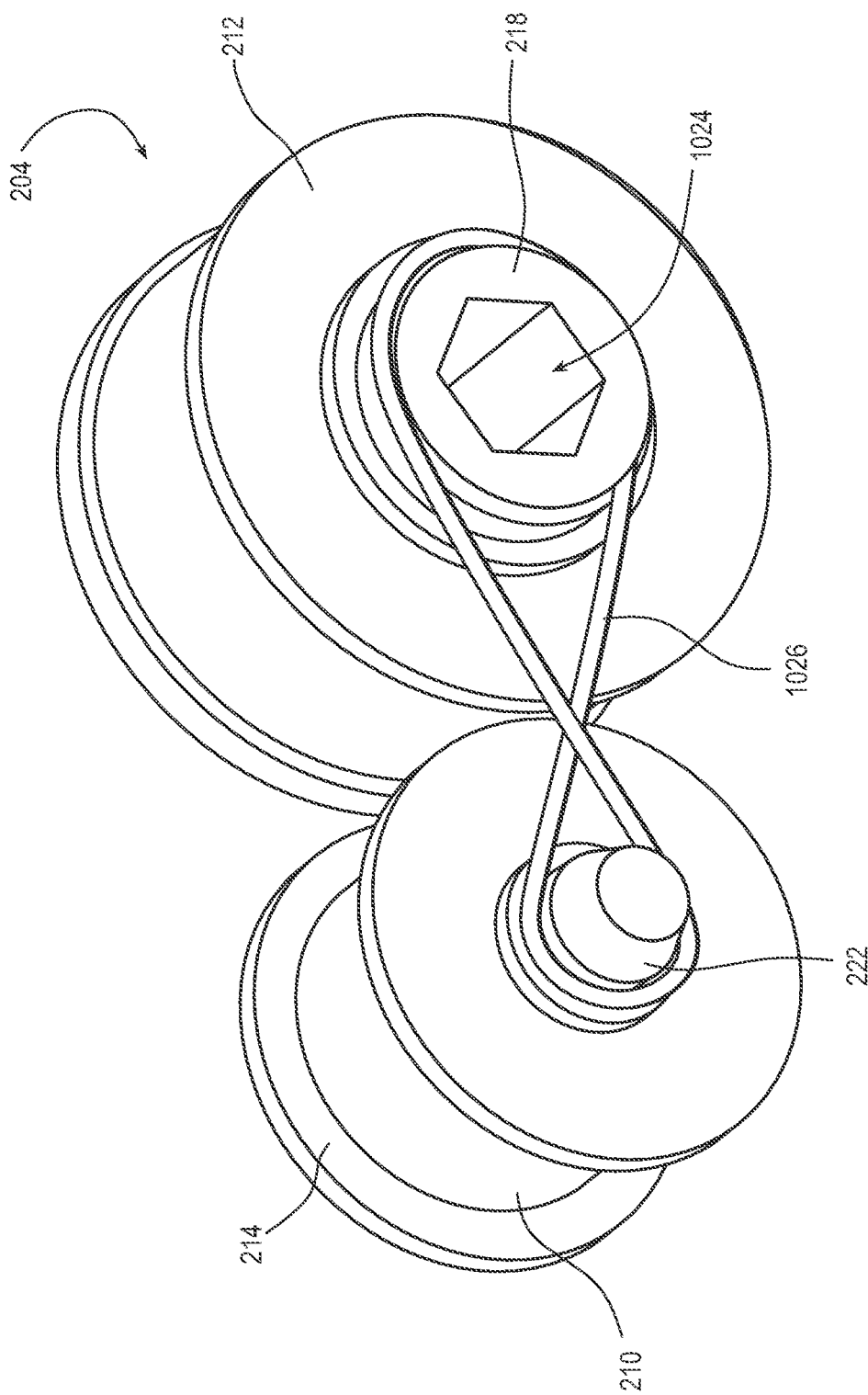
FIG. 10 illustrates the constant-torque spring assembly in accordance with some embodiments.
Figure 11:
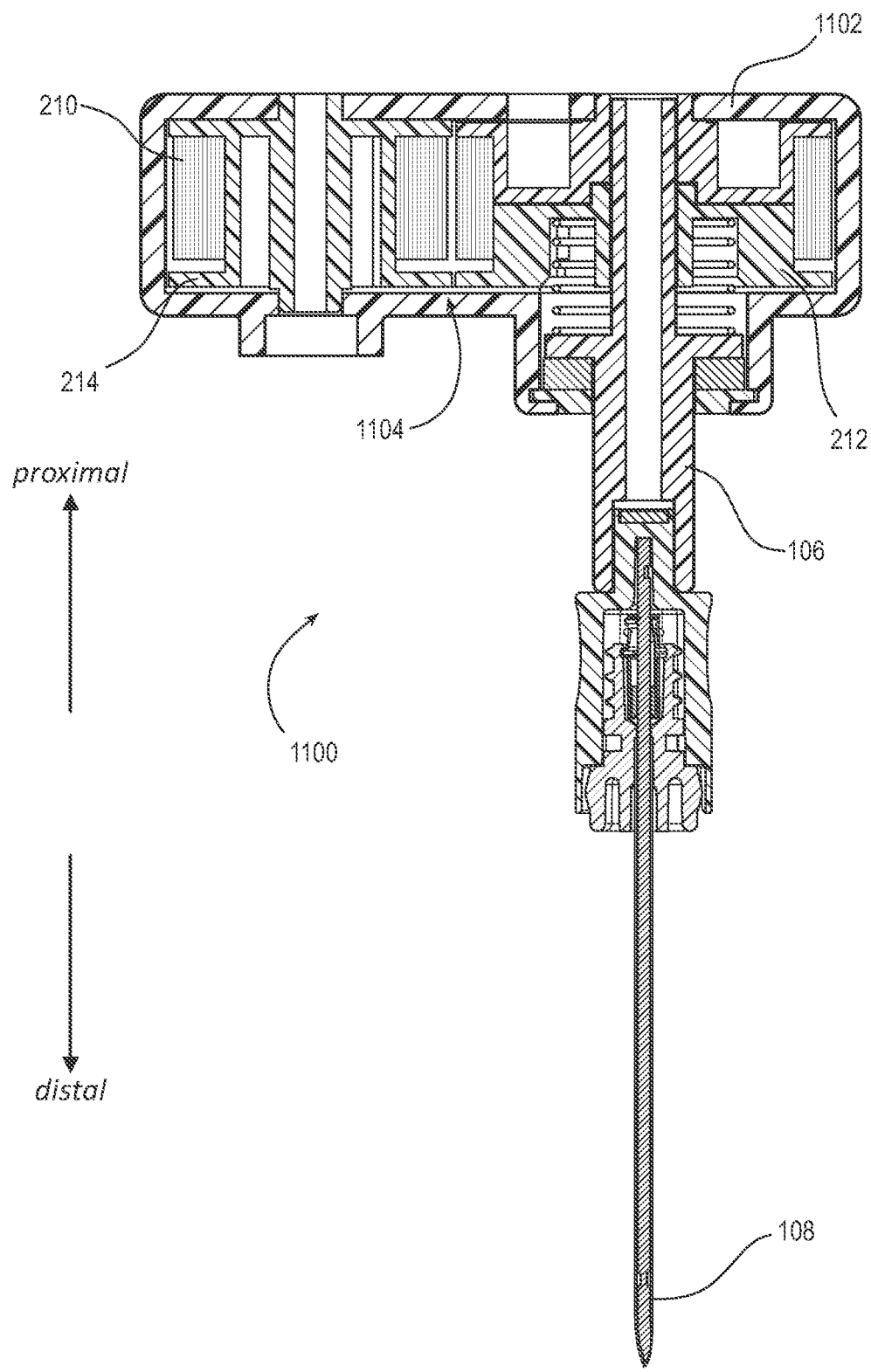
FIG. 11 illustrates a cross section of a third IO access device in accordance with some embodiments.
Figure 12:
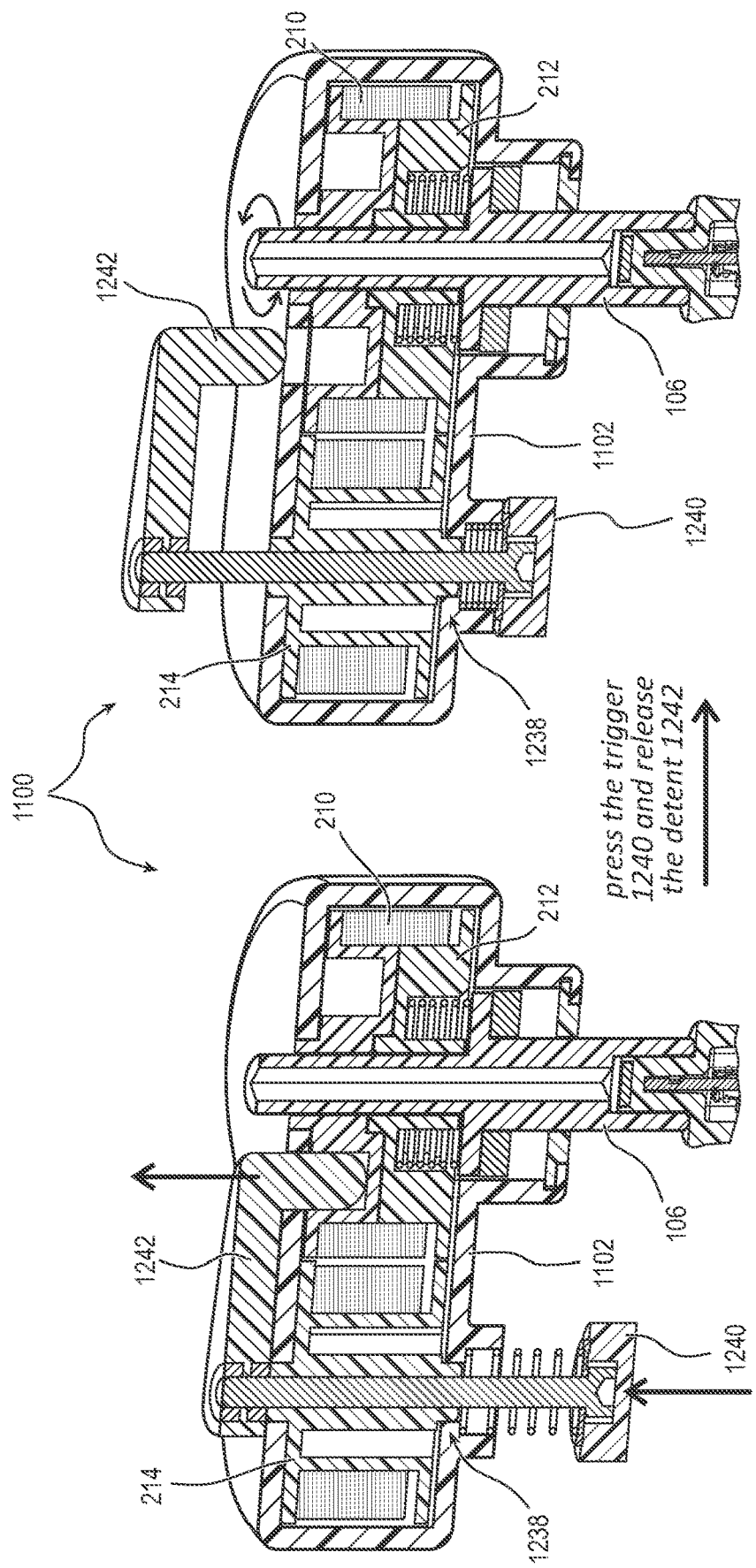
FIG. 12 illustrates a cross section of the third IO access device having a first interlock mechanism in accordance with some embodiments.
Figure 13:
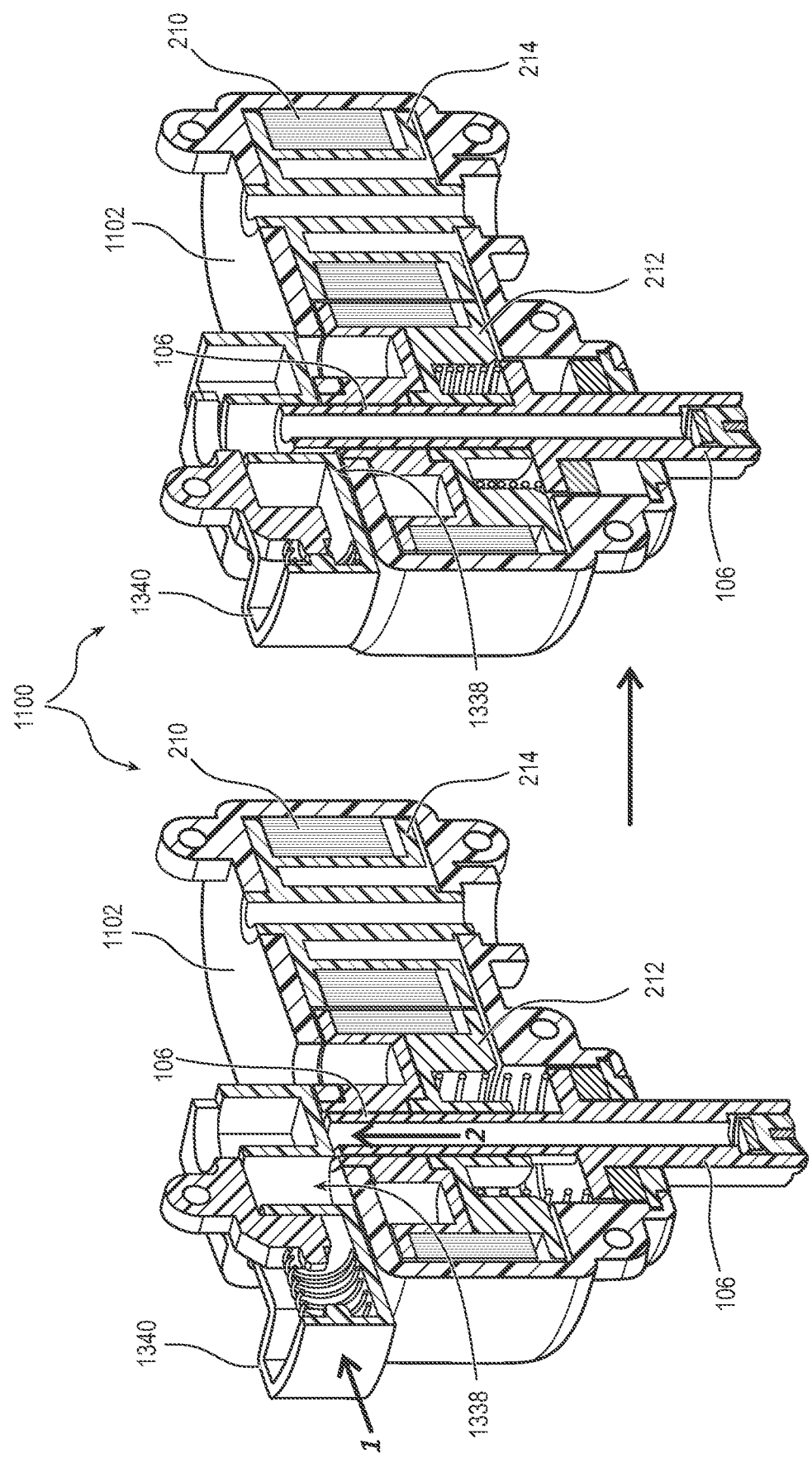
FIG. 13 illustrates a cross section of the third IO access device having a second interlock mechanism in accordance with some embodiments.

FIGS. 1-4 illustrate a first IO access device 100 in accordance with some embodiments. FIGS. 5-7 illustrate a second IO access device 500 in accordance with some embodiments. FIGS. 11-13 illustrate a third IO access device 1100 in accordance with some embodiments. FIG. 10 illustrates a constant-torque spring assembly 204 in accordance with some embodiments.

As shown, the IO access device 100, 500, or 1100 includes the constant-torque spring assembly 204, 604, or 1104 disposed a housing 102, 502, or 1102, a drive shaft 106 extending from the housing 102, 502, or 1102 and an IO needle assembly 108 coupled to the drive shaft 106 configured to provide IO access to a medullary cavity of a patient.

The housing 102, 502, or 1102 houses components of the IO access device 100, 500, or 1100. While the components of the IO access devices 100, 500, and 1100 are largely the same in terms of function, the components can be physically different in order to accommodate a particular form factor. For example, the IO access device 100 has a form factor for holding the IO access device 100 in a way that permits the IO needle assembly 108 to access a medullary cavity of a patient with a stabbing motion. In contrast, the IO access device 500 has a form factor for holding the IO access device 100 in a way that permits the IO needle assembly 108 to access a medullary cavity of a patient with in a more traditional drilling motion. The housing 102, 502, or 1102 is molded of a medically acceptable polymer such that sagittal halves of the housing 102, 502, or 1102 can be snapped or bound (e.g., mechanically fastened with fasteners, chemically bonded by adhesive, etc.) together around the components of the IO access device 100, 500, or 1100.

The constant-torque spring assembly 204, 604, or 1104 includes a metal ribbon (e.g., a stainless-steel ribbon) 210, at least a portion of which is reversely wound onto an output spool 212 and correctly wound onto a storage spool 214 with respect to a bias of the metal ribbon 210. The metal ribbon 210 is configured to wind onto the storage spool 214 or into a storage cavity with a constant torque across a range of revolutions-per-minute ("RPMs") when the output spool 212 is released or otherwise allowed to do so.

The constant-torque spring assembly 204, 604, or 1104 is unique in that stresses associated with deflection of the metal ribbon 210 are not cumulative over an entire length of the metal ribbon 210. The stresses are temporary and apply to only a short length (e.g., the exposed length) of the metal ribbon 210 at any given time. In addition, the metal ribbon 210 can be tuned with respect to any characteristic selected from its thickness, width, number of winds around the output spool 212, and the like for configuration of the constant-torque spring assembly 204, 604, or 1104 with an optimal rotary action of the IO needle assembly 108 for IO insertion.

Each spool of the output spool 212 and the storage spool 214 optionally includes a spindle co-incident with an axis of the spool for mounting the spool in the housing 102, 502, or 1102. Such a spindle can be on one side of the spool or both sides of the spool. For example, the constant-torque spring assembly 204 of the IO access device 100 includes spindle 216 and spindle 218 of the output spool 212 and spindle 220 and spindle 222 of the storage spool 214. Likewise, the constant-torque spring assembly 604 of the IO access device 500 includes spindle 616 and spindle 618 of the output spool 212 and spindle 620 and spindle 622 of the storage spool 214. The constant-torque spring assembly 1104 of the IO access device 1100 includes analogous spindles as well; however, reference number for the spindles are omitted for clarity.

Alternatively or additionally to the foregoing spindles, each spool of the output spool 212 and the storage spool 214 optionally includes an axial channel co-incident with the axis of the spool, which can be for mounting the spool in the housing 102, 502, or 1102, driving another component (e.g., the drive shaft 106) of the IO access device 100, 500, or 1100, etc. Such an axial channel can be in one side of the spool, both sides of the spool, or extending from one side of the spool to the other side of the spool. For example, the constant-torque spring assembly 204, 604, or 1104 of the IO access device 100, 500, or 1100 includes an axial channel 1024, which, in at least this case, includes a hexagonal shape to drive the hexagonal proximal-end portion of the drive shaft 106. (See FIGS. 9 and 10.) If the output spool 212 or the storage spool 214 includes a spindle on a side of the spool 212 or 214 and an axial channel in the same side of the spool 212 or 214, the spindle has an outer diameter large enough to accommodate an inner diameter of the axial channel as shown in FIG. 10 by the spindle 218 and the axial channel 1024.

As shown in FIG. 10, same-side spindles such as the spindles 218 and 222, respectively of the output spool 212 and the storage spool 214 of the constant-torque spring assembly 204, can be coupled together by at least one elastomeric loop 1026 (e.g., an 'O'-ring) to prevent any timing-related errors between the output spool 212 and the storage spool 214. Such timing-related errors are possible if the metal ribbon 210 winds onto the storage spool 214 more slowly than the metal ribbon 210 winds off the output spool 212—or vice versa. As shown, the elastomeric loop 1026 includes a half twist such that it crosses over itself to match the rotational motion of both the output spool 212 and the storage spool 214.

Notwithstanding the foregoing, the constant-torque spring assembly 204, 604, or 1104 can alternatively be configured as a constant-power spring assembly including a constant-power spring or a torsion spring assembly including a torsion spring. Like the constant-torque spring assembly 204, 604, or 1104 such a constant-power spring assembly or torsion spring assembly can be disposed in the housing 102, 502, or 1102 for driving the drive shaft 106 coupled to the IO needle assembly 108 to provide IO access to a medullary cavity of a patient.

The IO needle assembly 108 is configured to separate from the IO access device 100, 500, or 1100 subsequent to achieving IO access to a medullary cavity of a patient. While not shown, the IO needle assembly 108 includes an obturator removably disposed in a cannula. The cannula has a lumen configured for at least IO infusion upon removal of the obturator.

Pressure-Based Trigger Mechanism

Figure 8:
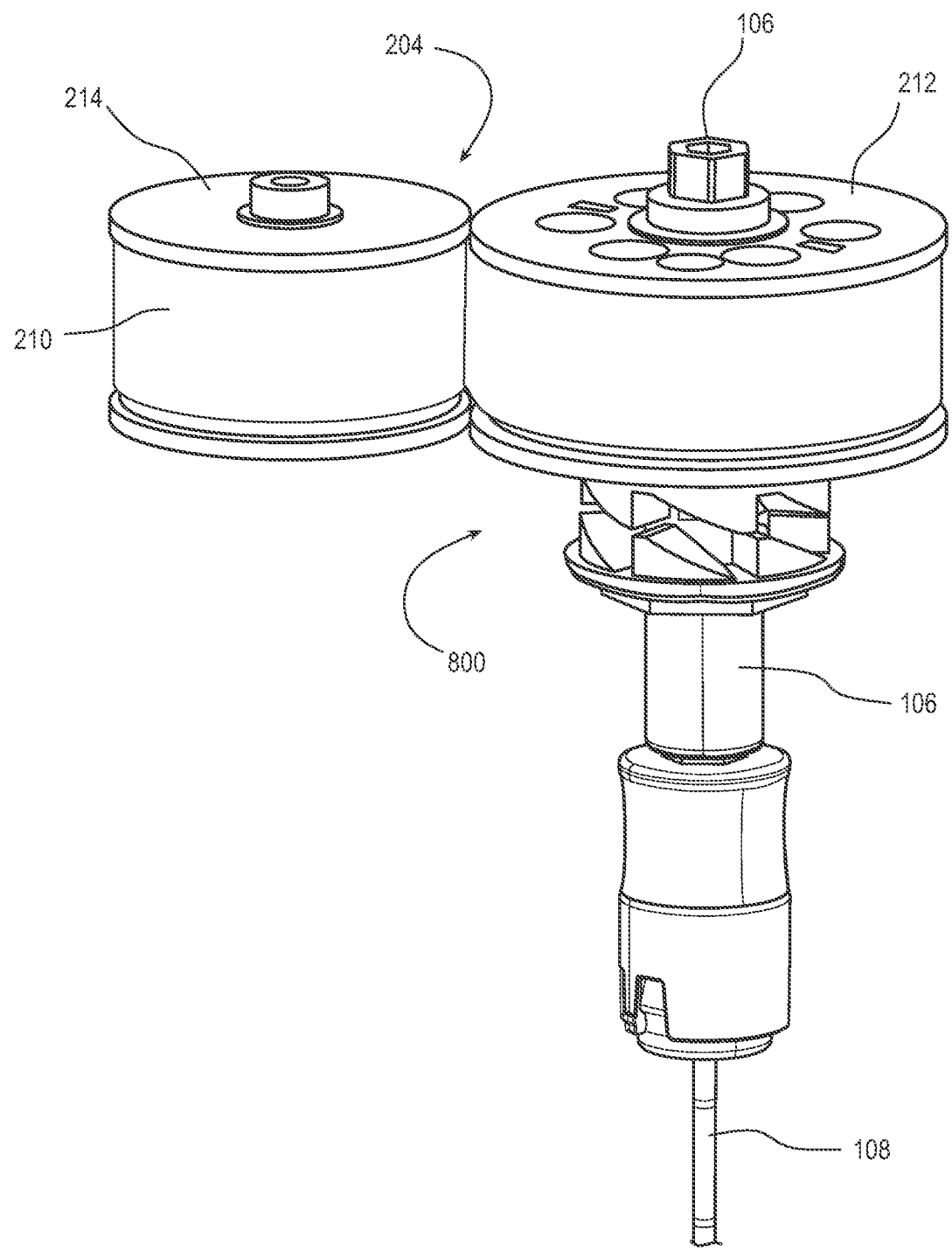
FIG. 8 illustrates a constant-torque spring assembly in combination with a pressure-based trigger mechanism in accordance with some embodiments.
Figure 9:
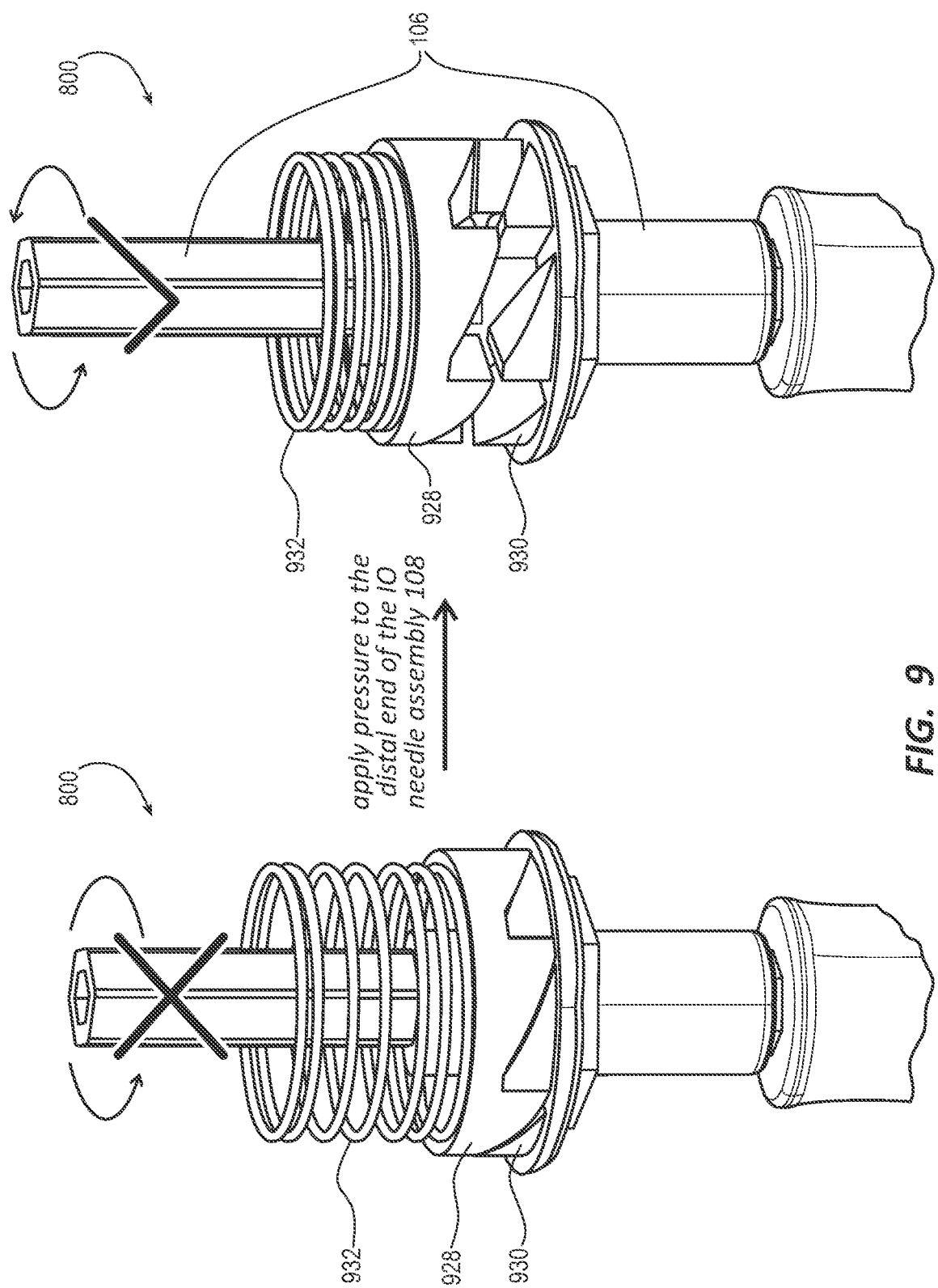
FIG. 9 illustrates different states of the pressure-based trigger mechanism in accordance with some embodiments.

FIG. 8 illustrates the constant-torque spring assembly 204 in combination with a pressure-based trigger mechanism 800 for activating rotation of the IO needle assembly 108 in accordance with some embodiments. FIG. 9 illustrates an inactive state and an active state of the pressure-based trigger mechanism 800 in accordance with some embodiments.

As shown, the pressure-based trigger mechanism 800 for activating rotation of the IO needle assembly 108 includes the drive shaft 106 slidably disposed in the axial channel 1024 of the output spool 212, a set of drive-shaft teeth 928 around the drive shaft 106, a set of opposing but complementary housing teeth 930 around an aperture of at least the housing 102 from which the drive shaft 106 extends, and a compression spring 932 between a back side of the set of drive-shaft teeth 928 and the output spool 212.

In the inactive state of at least the IO access device 100, a spring force is exerted on the back side of the set of drive-shaft teeth 928 by extension of the compression spring 932 between the back side of the set of drive-shaft teeth 928 and the output spool 212. Extension of the compression spring 932 keeps the drive shaft 106 pushed out of the axial channel 1024, which also keeps the set of drive-shaft teeth 928 thereof away from the output spool 212 such that the set of drive-shaft teeth 928 and the set of housing teeth 930 are engaged with each other. Each set of teeth of the set of drive-shaft teeth 928 and the set of housing teeth 930 can include sawtooth-shaped teeth. When such sets of teeth are engaged with each other as in the inactive state of the IO access device 100, rotation of the drive shaft 106 and, thus, the rotation of the IO needle assembly 108 is prevented.

In the active state of at least the IO access device 100, the spring force exerted on the back side of the set of drive-shaft teeth 928 by the extension of the compression spring 932 is overwhelmed by force applied to a distal-end portion of the drive shaft 106 by way of a distal end of the IO needle assembly 108. Compression of the compression spring 932 keeps the drive shaft 106 pushed into the axial channel 1024, which also keeps the set of drive-shaft teeth 928 thereof close to the output spool 212 such that the set of drive-shaft teeth 928 and the set of housing teeth 930 are disengaged with each other. When such sets of teeth are disengaged with each other as in the active state of the IO access device 100, rotation of the drive shaft 106 and, thus, the rotation of the IO needle assembly 108 is allowed.

In a transition between the inactive state and the active state of at least the IO access device 100, force applied to the distal-end portion of the drive shaft 106 by way of, for example, engaging bone with the distal end of the IO needle assembly 108, simultaneously inserts the drive shaft 106 deeper into the axial channel 1024 and compresses the compression spring 932 between the back side of the set of drive-shaft teeth 928 and the output spool 212. Inserting the drive shaft 106 deeper into the axial channel 1024 disengages the set of drive-shaft teeth 928 from the set of housing teeth 930 to initiate the active state of the IO access device 100, in which state rotation of the IO needle assembly 108 is effectuated by the output spool 212 of the constant-torque spring assembly 204 on the drive shaft 106.

In a transition between the active state and the inactive state of at least the IO access device 100, force removed from the distal-end portion of the drive shaft 106 by way of, for example, disengaging the distal end of the IO needle assembly 108 from bone, allows the compression spring 932 between the back side of the set of drive-shaft teeth 928 and the output spool 212 to relax, which pushes the drive shaft 106 out of the axial channel 1024 away from the output spool 212. Pushing the drive shaft 106 out of the axial channel 1024 reengages the set of drive-shaft teeth 928 with the set of housing teeth 930 to initiate the inactive state of the IO access device 100, in which state rotation of the IO needle assembly 108 is by the output spool 212 of the constant-torque spring assembly 204 on the drive shaft 106 is prevented.

The transition between the active state and the inactive state of at least the IO access device 100 can be automatically initiated by the IO access device 100. In such an IO access device, the compression spring 932 is configured by way of its material, construction, or both to have a spring constant and a compressible length proportional to a spring force greater than an average force that can be applied on the distal end of the IO needle assembly 108 by marrow in a medullary cavity of a patient. Entry of the IO needle assembly 108 into the medullary cavity of the patient automatically replaces the force applied on the distal end of the IO needle assembly 108 by compact bone, which force is greater than the foregoing spring force, with the force applied on the distal end of the IO needle assembly 108 by the marrow in the medullary cavity, which force is less than the foregoing spring force, thereby allowing the compression spring 932 to push the drive shaft 106 out of the axial channel 1024 away from the output spool 212 to initiate the transition to the inactive state of the IO access device 100. Notwithstanding the foregoing, the transition between the active state and the inactive state can be manually initiated by a clinician after feeling a change in tissue density upon entering the medullary cavity from compact bone.

While the pressure-based trigger mechanism 800 is described for the IO access device 100, it should be understood that any IO access device selected from the IO access devices 100, 500 and 1100 can include the pressure-based trigger mechanism 800, optionally as part of an interlock mechanism. Notably, the IO access devices 500 and 1100 are not shown with the set of drive-shaft teeth 928 or the complementary set of housing teeth 930 of the pressure-based trigger mechanism 800. Without such teeth, rotation of the IO needle assembly 108 must be effectuated by or in combination with another rotation-activating means set forth herein for activating rotation of the IO needle assembly 108. Notwithstanding that, the compression spring 932 remains a useful component to a clinician for feeling the change in tissue density upon the distal end of the IO needle assembly 108 entering the medullary cavity from compact bone, thereby signaling drilling should be stopped. Indeed, regardless of whether the IO access device 500 or 1100 includes the set of drive-shaft teeth 928 and the set of housing teeth 930, the compression spring 932 is still configured to push the drive shaft 106 out of the axial channel 1024 away from the output spool 212 upon the distal end of the IO needle assembly 108 entering the medullary cavity from compact bone, which provides an immediate palpable signal to a clinician to stop drilling.

Force-Decoupling Mechanism

Figure 2:
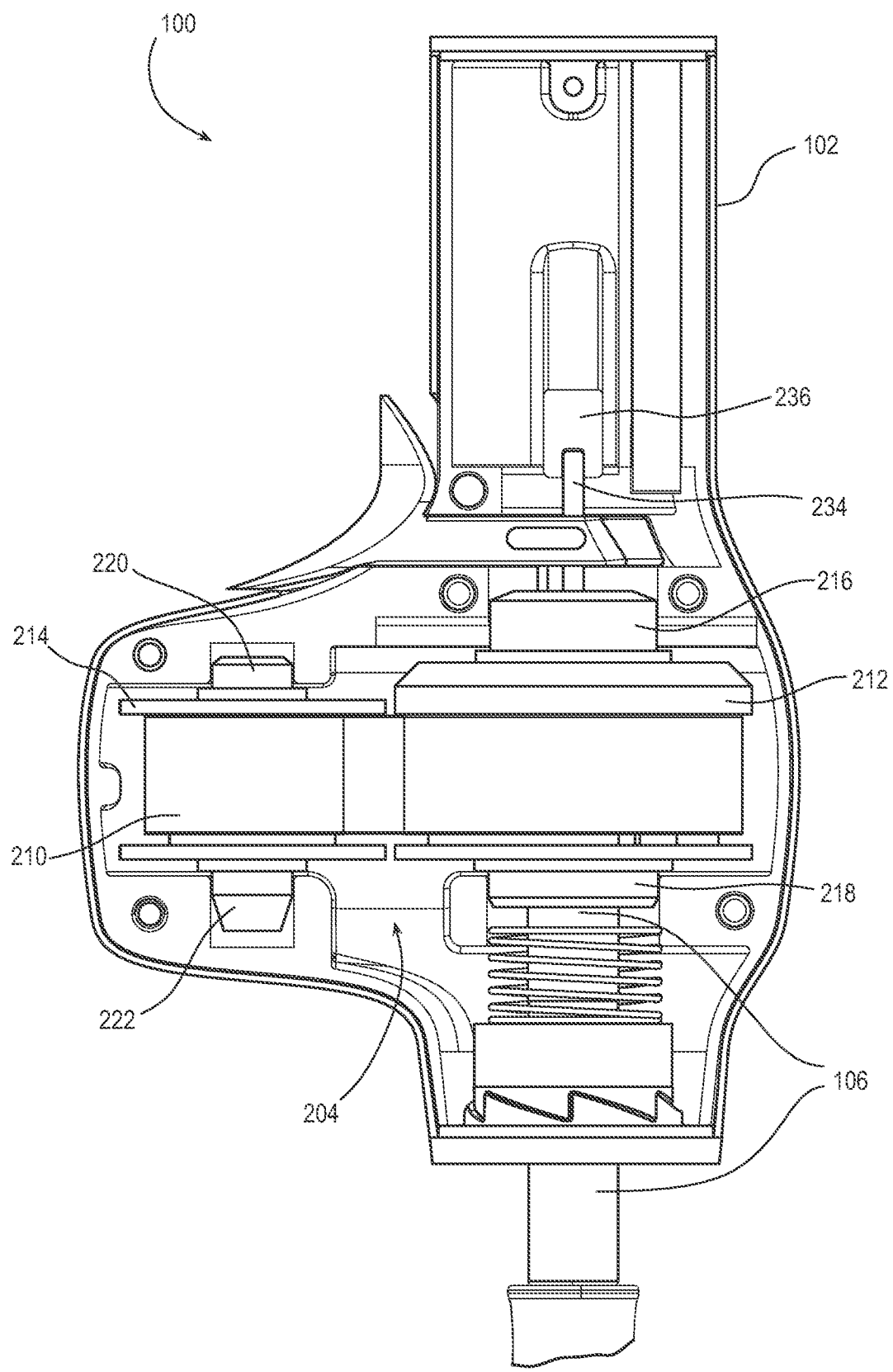
FIG. 2 illustrates the first IO access device with a side of housing removed in accordance with some embodiments.

As shown in FIG. 2 for at least the IO access device 100, a combination of an extension pin 234 disposed in the axial channel 1024 of the output spool 212 between the drive shaft 106 and a molded piece 236 within the housing 102 is configured to stop over insertion of the drive shaft 106 into the axial channel 1024 of the output spool 212 during the transition between the inactive state and the active state of the IO access device 100. In addition to stopping the over insertion of the drive shaft 106 into the axial channel 1024 of the output spool 212, the combination of the extension pin 234 and the molded piece 236 provides a decoupling mechanism configured to decouple the force applied to the distal end of the IO needle assembly 108 from the constant-torque spring assembly 204. That is, any further force applied to the distal end of the IO needle assembly 108 than that needed for the transition between the inactive state and the active state of at least the IO access device 100 is applied to the molded piece 236 of the housing 102 by the extension pin 234 instead of the constant-torque spring assembly 204. Minimization of bearing surface area and reduction of extraneous moment-arm lengths further decouple the force applied to the distal end of the IO needle assembly 108 from the constant-torque spring assembly 204.

Interlock Mechanisms

Figure 3:
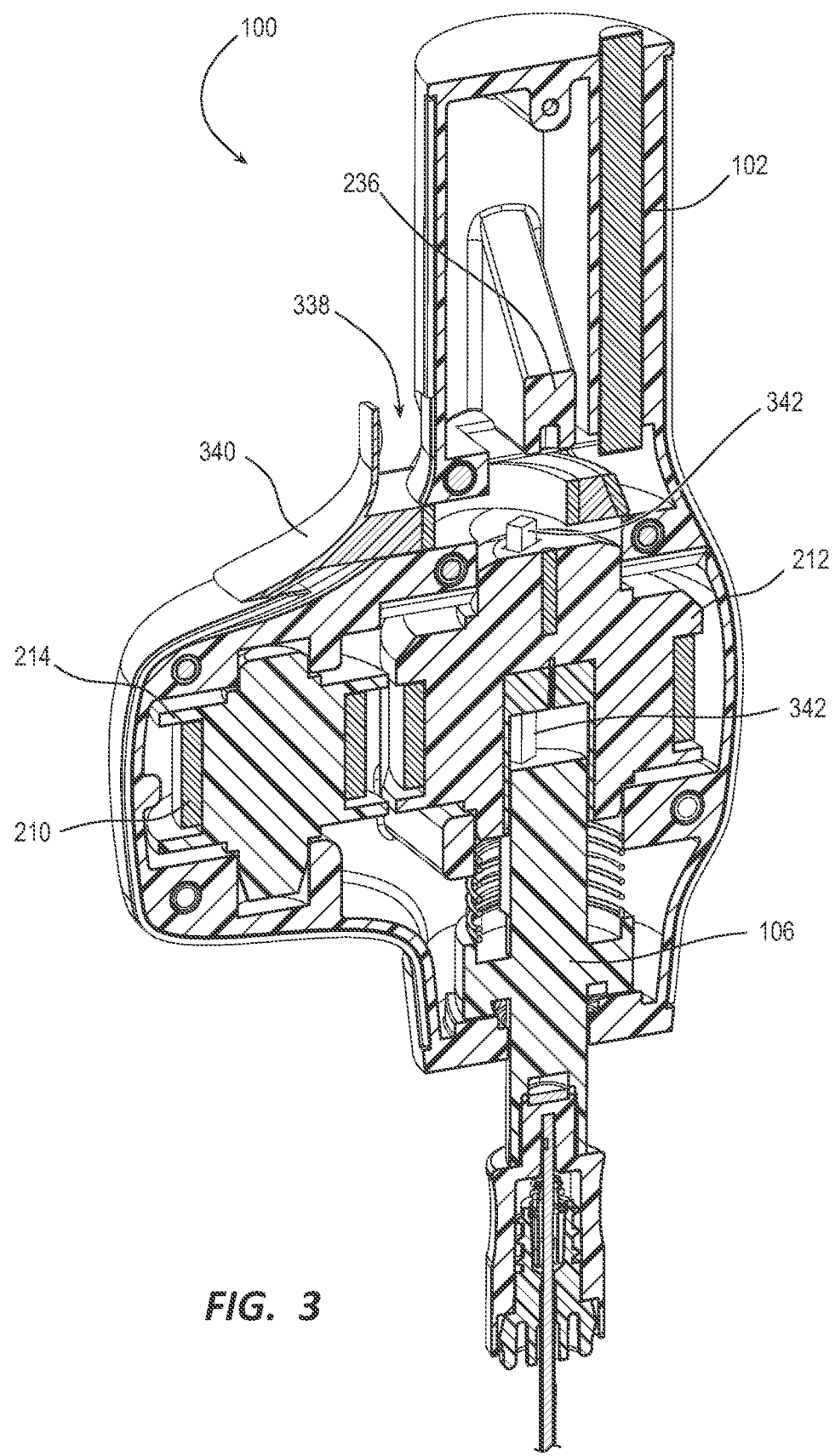
FIG. 3 illustrates a cross section of the first IO access device having a first interlock mechanism in accordance with some embodiments.

FIG. 3 illustrates a cross section of the IO access device 100 having a first interlock mechanism 338 in accordance with some embodiments.

As shown in FIG. 3, the interlock mechanism 338 of the IO access device 100 includes a trigger 340 and a lock pin 342 disposed between the trigger 340 and the output spool 212 in the inactive state of the IO access device 100. The interlock mechanism 338 must be disengaged before the pressure-based trigger mechanism 800 can be activated for rotation of the IO needle assembly 108, thereby providing a safety mechanism for the IO access device 100. The trigger 340 can be pressed with a clinician's fingers, web of his or her hand, or the like such as by gripping the IO access device 100. When the trigger 340 is pressed in toward the housing 102, the trigger 340 is configured to release the lock pin 342. Once released, the lock pin 342 is free to move in a proximal direction when a force is applied to the distal end of the IO needle assembly 108 that simultaneously compresses the compression spring 932 and inserts the drive shaft 106 deeper into the axial channel 1024.

Figure 4:
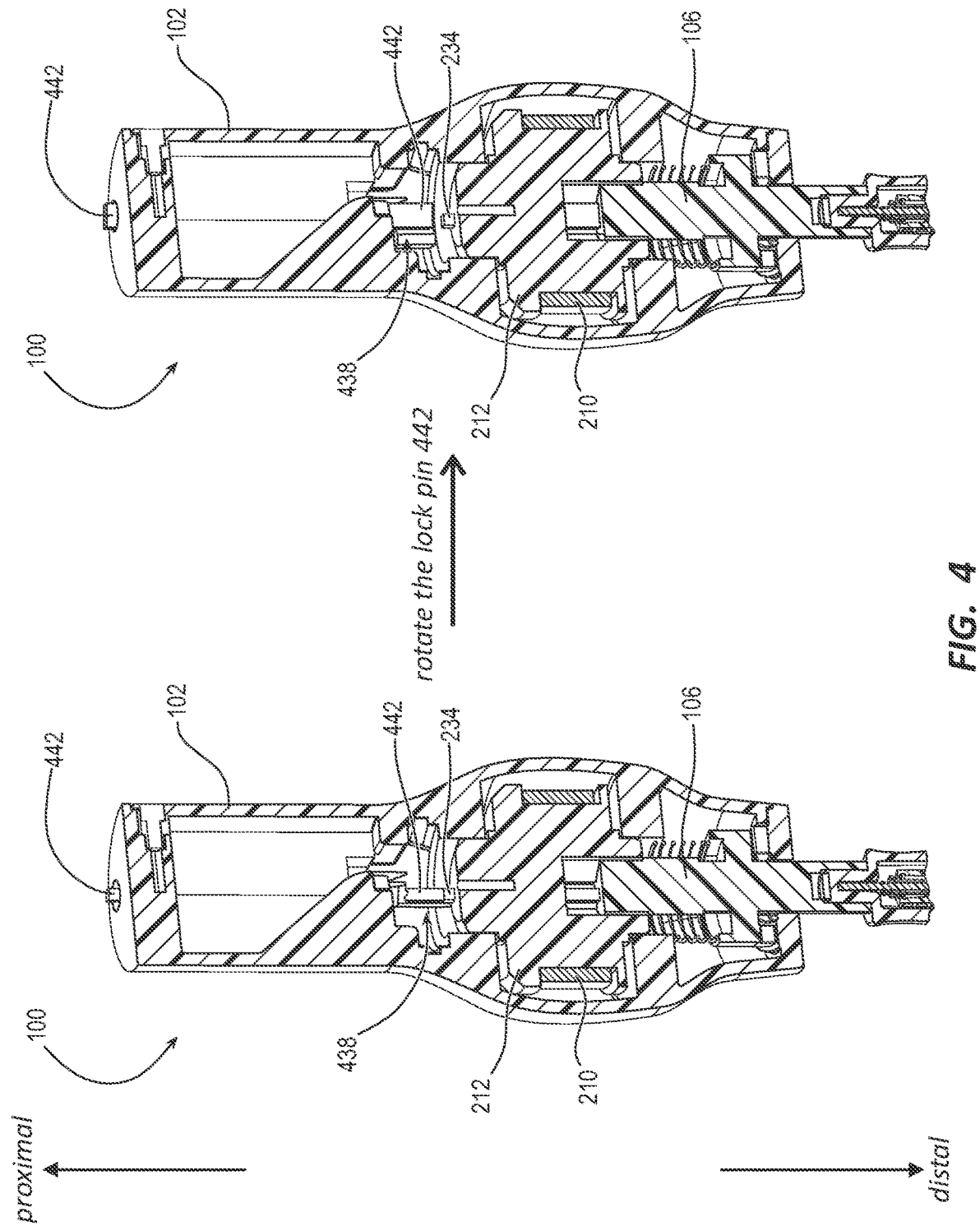
FIG. 4 illustrates a cross section of the first IO access device having a second interlock mechanism in accordance with some embodiments.

FIG. 4 illustrates a cross section of the IO access device 100 having a second interlock mechanism 438 in accordance with some embodiments.

As shown, the interlock mechanism 438 includes a lock pin 442 configured to rotate such that the lock pin 442 does not block axial movement of the extension pin 234 in the axial channel 1024 of the output spool 212, thereby allowing activation of the pressure-based trigger mechanism 800.

This is shown on the right-hand side of FIG. 4, wherein the lock pin 442 is no longer engaged with the extension pin 234.

FIG. 7 illustrates a cross section of the IO access device 500 having an interlock mechanism 738 in accordance with some embodiments.

As shown in FIG. 7, the interlock mechanism 738 of the IO access device 500 includes a trigger 640 pivotally mounted on a transversely oriented pin 642 disposed in the housing 502 adjacent the output spool 212. Both an internal-end portion of the trigger 640 and a distal-end portion of the output spool 212 have interlocking teeth that are interlocked in the inactive state of the IO access device 500. The interlock mechanism 738 must be disengaged before the pressure-based trigger mechanism 800 can be activated for rotation of the IO needle assembly 108, thereby providing a safety mechanism for the IO access device 500. When an external-end portion of the trigger 640 is pressed in toward the housing 502, the trigger 640 is configured to pivot about the pin 642 and withdraw the interlocking teeth of the internal-end portion of the trigger 640 away from those of the output spool 212, thereby allowing a force applied to the distal end of the IO needle assembly 108 to simultaneously compress the compression spring 932 and insert the drive shaft 106 deeper into the axial channel 1024 for rotation of the IO needle assembly 108.

FIG. 12 illustrates a cross section of the third IO access device 1100 having a first interlock mechanism 1238 in accordance with some embodiments.

As shown on the left-hand side of FIG. 12, the pressure-based trigger mechanism 800 of the IO access device 1100 is activated, but a detent 1242 coupled to a spring-mounted trigger 1240 of the interlock mechanism 1238 is engaged with a bore of the output spool 212 preventing rotation of the IO needle assembly 108. This is mechanistically different than any interlock mechanism of the interlock mechanisms 338, 438, and 738, which require the interlock mechanism 338, 438, or 738, to be disengaged before the pressure-based trigger mechanism 800 can even be activated. Indeed, the IO access device 1100 is configured such that either the interlock mechanism 1238 or the pressure-based trigger mechanism 800 can be activated first, but both the pressure-based trigger mechanism 800 and the interlock mechanism 1238 need to be activated for rotation of the IO needle assembly 108. When the trigger 1240 is pressed in toward the housing 1102, the detent 1242 is configured to withdraw from the bore of the output spool 212, thereby allowing—if a force is already applied to the distal end of the IO needle assembly 108—the applied force to simultaneously compress the compression spring 932 and insert the drive shaft 106 deeper into the axial channel 1024 for rotation of the IO needle assembly 108. The IO access device with the interlock mechanism is configured such that rotation of the IO needle assembly 108 can be interrupted at any time by removing the pressure applied to the distal end of the IO needle assembly 108 or releasing the trigger 1240, which relaxes the spring of the spring-loaded trigger 1240 returning the trigger to its default position.

FIG. 13 illustrates a cross section of the third IO access device 1100 having a second interlock mechanism 1338 in accordance with some embodiments.

As shown in FIG. 13, the interlock mechanism 1338 of the IO access device 1100 includes a spring-loaded trigger 1340 slidably mounted in an exterior channel of the housing 1102 proximal of the output spool 212. The trigger 1340 includes an extension channel of the axial channel 1024. When the trigger 1340 is activated and properly aligned, the drive shaft 106 can extend into the extension channel of the trigger 1340 upon application of force to the distal-end portion of the drive shaft 106 in accordance with activation of the pressure-based trigger mechanism 800. When the trigger 1340 is not activated or not properly aligned, the drive shaft 106 cannot extend into the extension channel of the trigger 1340, which precludes activation of the pressure-based trigger mechanism 800. That is, the interlock mechanism 1338 must be disengaged before the pressure-based trigger mechanism 800 can be activated for rotation of the IO needle assembly 108, thereby providing a safety mechanism for the IO access device 1100.

As an additional preventing means to the foregoing interlock mechanisms 338, 438, 738, 1238, and 1338 for preventing accidental activation of the pressure-based trigger mechanism 800 of an IO access device by dropping or handling the IO access device, a needle cover can be included to cover the IO needle assembly 108. While not shown, the needle cover is configured to cover the IO needle assembly 108 and prevent accidental activation of the pressure-based trigger mechanism 800 by way of providing a spatial buffer around the IO needle assembly 108. Until the needle cover is removed from around the IO needle assembly 108, a clinician is also prevented from touching the IO needle assembly 108, thereby enhancing sterility of the IO needle assembly 108.

Braking Mechanism

While not shown, the IO access device 100, 500, or 1100 can further include a hand-actuated braking system configured to act on the output spool 212 to slow the metal ribbon 210 from winding onto the storage spool 214. The braking system can be initiated at a start of the winding of the metal ribbon 210 onto the storage spool 214 or at any time throughout the winding.

Methods

Methods of the IO access device 100, 500, or 1100 include at least a method of using the IO access device 100, 500, or 1100.

A method of using the IO access device 100, 500, or 1100 includes at least a device-obtaining step. The device-obtaining step includes obtaining the IO access device 100, 500, or 1100.

The method can also include a skin-preparing step. The skin-preparing step includes preparing skin of a patient with an antiseptic (e.g., iodopovidone) at an insertion site of the patient. The insertion site can be about the proximal tibia, the distal tibia, or the distal femur.

The method can also include an interlock-disengaging step. The interlock-disengaging step includes disengaging an interlock mechanism set forth herein configured to prevent rotation of an IO needle and drilling therewith until the interlock mechanism is disengaged. In an example, the interlock-disengaging step can include triggering the trigger 340 to release the lock pin 342 disposed between the trigger 340 and the output spool 212. In another example, the interlock-disengaging step can include rotating the lock pin 442 configured to block axial movement of the extension pin 234 disposed in the axial channel 1024 of the output spool 212 between the lock pin 442 and the drive shaft 106. In yet another example, the interlock-disengaging step can include triggering the trigger 640 pivotally mounted on the transversely oriented pin 642 having trigger teeth configured to interlock with those of a distal-end portion of the output spool 212. In yet another example, the interlock-disengaging step can include triggering the spring-loaded trigger 1340 mounted in the exterior channel of the housing 1102 including the extension channel configured to allow the drive shaft 106 to extend from the axial channel 1024 of the output spool 212 into the extension channel when the extension channel and the axial channel 1024 are aligned. The pressure-based trigger mechanism 800 is configured to require the foregoing interlock-disengaging step before the force-applying step to activate the pressure-based trigger mechanism. That said the pressure-based trigger mechanism 800 can be configured to require the interlock-disengaging step either before or after the force-applying step to activate the pressure-based trigger mechanism. Indeed, the interlock-disengaging step can include triggering the pressure-based trigger 1240 configured to release the detent 1242 from the bore of the output spool 212.

The method can also include a needle-inserting step. The needle-inserting step includes inserting the distal end of the IO needle of the IO needle assembly 108 through the skin at the insertion site.

The method can also include a force-applying step. The force-applying step includes applying force to bone at the insertion site with the distal end of the IO needle of the IO needle assembly 108 to activate the pressure-based trigger mechanism 800. In accordance with force-applying step, the drive shaft 106 is inserted deeper into the axial channel 1024 of the output spool 212 of the constant-torque spring assembly 204, 604, or 1104, which compresses the compression spring 932 between the back side of the set of drive-shaft teeth 928 and the output spool 212. Compressing the compression spring 932 disengages the set of drive-shaft teeth 928 from the opposing set of housing teeth 930 around the aperture of the housing 102, 502, or 1102. Further in accordance with the force-applying step, the metal ribbon 210 of the constant-torque spring assembly 204, 604, or 1104 starts winding from the output spool 212 onto the storage spool 214, thereby starting rotation of the IO needle assembly 108 and the IO needle thereof by way of the drive shaft 106 coupled to the constant-torque spring assembly 204, 604, or 1104.

The method can also include a drilling step. The drilling step includes drilling through the bone until the IO needle assembly 108 enters a medullary cavity of the patient. IO access is achieved upon entering the medullary cavity of the patient with the IO access device 100, 500, or 1100.

The method can also include a force-ceasing step. The force-ceasing step includes ceasing to apply the force to the bone with the distal end of the IO needle assembly 108 or the IO needle thereof. The force-ceasing step removes at least a portion of the drive shaft 106 from the axial channel 1024 of the output spool 212, relaxes the compression spring 932, and reengages the set of drive-shaft teeth 928 with the set of housing teeth 930 to stop the rotation of the IO needle assembly 108. The force-ceasing step can be automatically initiated by the IO access device 100, 500, or 1100 after experiencing a change in tissue density (e.g., compact bone to marrow) upon entering the medullary cavity of the patient. Alternatively, the force-ceasing step can be manually initiated by a clinician after feeling the change in tissue density upon entering the medullary cavity of the patient.

The method can also include a needle-detaching step. The needle-detaching step includes detaching the IO needle assembly 108 from a remainder of the IO access device 100, 500, or 1100.

The method can also include an obturator-removing step. The obturator-removing step includes removing from the IO needle assembly 108 the obturator removably disposed in a cannula.

The method can also include a cannula-confirming step. The cannula-confirming step includes confirming the cannula is disposed in the medullary cavity by aspirating bone marrow through a syringe.

The method can also include a cannula-securing step. The cannula-securing step includes securing the cannula to the patient with a dressing.

The method can also include an infusion-starting step. The infusion-starting step includes starting IO infusion as boluses with a same or different syringe.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An intraosseous access device, comprising:
a constant-torque spring assembly disposed in a housing;
a drive shaft extending from the housing, the drive shaft coupled to the constant-torque spring assembly;
an intraosseous needle coupled to the drive shaft configured for drilling through bone and providing intraosseous access to a medullary cavity of a patient; and
an interlock mechanism configured to prevent rotation of the intraosseous needle and the drilling therewith until the interlock mechanism is disengaged.

2. The intraosseous access device of claim 1, wherein the constant-torque spring assembly includes a metal ribbon reversely wound onto an output spool having an axial channel, the metal ribbon configured to wind onto a storage spool with a constant torque when the output spool is released.

3. The intraosseous access device of claim 2, wherein spindles of the output spool and the storage spool are coupled together by at least one elastomeric loop to prevent any timing-related errors between the output spool and the storage spool.

4. The intraosseous access device of claim 2, wherein the interlock mechanism includes a trigger configured to release a lock pin disposed between the trigger and the output spool, a pressure-based trigger mechanism of the intraosseous access device configured to require the interlock mechanism to be disengaged before activation of the pressure-based trigger mechanism for rotation of the intraosseous needle.

5. The intraosseous access device of claim 2, wherein the interlock mechanism includes a rotatable lock pin configured to block axial movement of an extension pin disposed in the axial channel of the output spool between the lock pin and the drive shaft, a pressure-based trigger mechanism of the intraosseous access device configured to require the interlock mechanism to be disengaged before activation of the pressure-based trigger mechanism for rotation of the intraosseous needle.

6. The intraosseous access device of claim 2, wherein the interlock mechanism includes a trigger pivotally mounted on a transversely oriented pin having trigger teeth configured to interlock with those of a distal-end portion of the output spool, a pressure-based trigger mechanism of the intraosseous access device configured to require the interlock mechanism to be disengaged before activation of the pressure-based trigger mechanism for rotation of the intraosseous needle.

7. The intraosseous access device of claim 2, wherein the interlock mechanism includes a spring-loaded trigger mounted in an exterior channel of the housing including an extension channel configured to allow the drive shaft to extend from the axial channel into the extension channel when the extension channel and the axial channel are aligned, a pressure-based trigger mechanism of the intraosseous access device configured to require the interlock mechanism to be disengaged before activation of the pressure-based trigger mechanism for rotation of the intraosseous needle.

8. The intraosseous access device of claim 2, wherein the interlock mechanism includes a pressure-based trigger configured to release a detent from a bore of the output spool, a pressure-based trigger mechanism of the intraosseous access device configured to allow the interlock mechanism to be disengaged either before or after activation of the pressure-based trigger mechanism for rotation of the intraosseous needle.

9. The intraosseous access device of claim 4, wherein the pressure-based trigger mechanism includes a set of housing teeth around an aperture of the housing from which the drive shaft extends and a set of complementary drive-shaft teeth around the drive shaft opposing the set of housing teeth, the set of housing teeth and the set of drive-shaft teeth engaged in an inactive state of the intraosseous access device by a compression spring between a back side of the set of drive-shaft teeth and the output spool.

10. The intraosseous access device of claim 9, wherein the drive shaft is slidably disposed in the axial channel of the output spool such that force applied to a distal end of the intraosseous needle simultaneously compresses the compression spring and inserts the drive shaft deeper into the axial channel, thereby disengaging the set of drive-shaft teeth from the set of housing teeth and initiating an active state of the intraosseous access device in which rotation of the intraosseous needle is effectuated by the output spool of the constant-torque spring assembly on the drive shaft.

11. The intraosseous access device of claim 10, wherein the compression spring is configured to relax when the force applied to the distal end of the intraosseous needle is removed, thereby reengaging the set of drive-shaft teeth with the set of housing teeth and reinitiating the inactive state of the intraosseous access device.

12. The intraosseous access device of claim 10, wherein the intraosseous access device is configured such that entry of the intraosseous needle into the medullary cavity of the patient automatically removes the force applied to the distal end of the intraosseous needle.

13. The intraosseous access device of claim 2, further comprising a braking system configured to act on the output spool to slow the metal ribbon from winding onto the storage spool.

14. The intraosseous access device of claim 1, wherein the intraosseous needle is configured to separate from the intraosseous access device subsequent to achieving intraosseous access to the medullary cavity of the patient.

15. The intraosseous access device of claim 1, wherein the intraosseous needle includes an obturator removably disposed in a cannula having a lumen configured for at least intraosseous infusion upon removal of the obturator.

16. A method of an intraosseous access device, comprising:
obtaining the intraosseous access device;
disengaging an interlock mechanism configured to prevent rotation of an intraosseous needle and drilling therewith until the interlock mechanism is disengaged;
inserting a distal end of the intraosseous needle through skin at an insertion site of a patient;
applying force to bone at the insertion site with the distal end of the intraosseous needle to activate a pressure-based trigger mechanism and start winding a metal ribbon of a constant-torque spring assembly from an output spool onto a storage spool, thereby starting rotation of the intraosseous needle by way of a drive shaft coupled to the constant-torque spring assembly; and
drilling through the bone until the intraosseous needle enters a medullary cavity of the patient, thereby achieving intraosseous access to the medullary cavity of the patient with the intraosseous access device.

17. The method of claim 16, wherein disengaging the interlock mechanism includes triggering a trigger to release a lock pin disposed between the trigger and the output spool, the pressure-based trigger mechanism configured to require the disengaging of the interlock mechanism before applying force to the bone at the insertion site activates the pressure-based trigger mechanism.

18. The method of claim 16, wherein disengaging the interlock mechanism includes rotating a lock pin configured to block axial movement of an extension pin disposed in an axial channel of the output spool between the lock pin and the drive shaft, the pressure-based trigger mechanism configured to require the disengaging of the interlock mechanism before applying force to the bone at the insertion site activates the pressure-based trigger mechanism.

19. The method of claim 16, wherein disengaging the interlock mechanism includes triggering a trigger pivotally mounted on a transversely oriented pin having trigger teeth configured to interlock with those of a distal-end portion of the output spool, the pressure-based trigger mechanism configured to require the disengaging of the interlock mechanism before applying force to the bone at the insertion site activates the pressure-based trigger mechanism.

20. The method of claim 16, wherein disengaging the interlock mechanism includes triggering a spring-loaded trigger mounted in an exterior channel of a housing including an extension channel configured to allow the drive shaft to extend from an axial channel of the output spool into the extension channel when the extension channel and the axial channel are aligned, the pressure-based trigger mechanism configured to require the disengaging of the interlock mechanism before applying force to the bone at the insertion site activates the pressure-based trigger mechanism.

21. The method of claim 16, wherein disengaging the interlock mechanism includes triggering a pressure-based trigger configured to release a detent from a bore of the output spool, the pressure-based trigger mechanism configured to require the disengaging of the interlock mechanism either before or after applying force to the bone at the insertion site activates the pressure-based trigger mechanism.

22. The method of claim 16, further comprising ceasing to apply the force to the bone with the distal end of the intraosseous needle, thereby stopping rotation of the intraosseous needle.

23. The method of claim 22, wherein ceasing to apply the force to the bone with the distal end of the intraosseous needle is manually initiated by a clinician after feeling a change in tissue density upon entering the medullary cavity of the patient or automatically initiated by the pressure-based trigger mechanism after the change in the tissue density upon entering the medullary cavity of the patient.

24. The method of claim 16, further comprising:
detaching the intraosseous needle from a remainder of the intraosseous access device;
removing from the intraosseous needle an obturator removably disposed in a cannula;
confirming the cannula is disposed in the medullary cavity by aspirating bone marrow through a syringe;
securing the cannula to the patient; and
starting intraosseous infusion as boluses with a same or different syringe.

* * * * *